US009598699B2

(12) United States Patent
Umemoto et al.

(10) Patent No.: US 9,598,699 B2
(45) Date of Patent: Mar. 21, 2017

(54) PROTEIN HAVING GLYCOALKALOID BIOSYNTHETIC ENZYME ACTIVITY AND GENE ENCODING THE SAME

(75) Inventors: Naoyuki Umemoto, Sakura (JP); Katsunori Sasaki, Sakura (JP)

(73) Assignee: KIRIN HOLDINGS KOBUSHIKI KAISHA, Tokyo (JP)

(*) Notice: Subject to any disclaimer, the term of this patent is extended or adjusted under 35 U.S.C. 154(b) by 0 days.

(21) Appl. No.: 13/392,790

(22) PCT Filed: Aug. 30, 2010

(86) PCT No.: PCT/JP2010/064744
§ 371 (c)(1),
(2), (4) Date: Feb. 27, 2012

(87) PCT Pub. No.: WO2011/025011
PCT Pub. Date: Mar. 3, 2011

(65) Prior Publication Data
US 2012/0159676 A1   Jun. 21, 2012

(30) Foreign Application Priority Data

Aug. 28, 2009  (JP) ................................ 2009-198889
May 10, 2010  (JP) ................................ 2010-108445

(51) Int. Cl.
C12N 15/82 (2006.01)
C07K 14/415 (2006.01)
C12N 9/00 (2006.01)
C12N 9/02 (2006.01)
C12Q 1/68 (2006.01)

(52) U.S. Cl.
CPC ........ *C12N 15/8243* (2013.01); *C07K 14/415* (2013.01); *C12N 9/00* (2013.01); *C12N 9/0071* (2013.01); *C12Q 1/6895* (2013.01); *C12Y 114/14001* (2013.01); *C12Q 2600/156* (2013.01)

(58) Field of Classification Search
USPC ........................................................ 800/278
See application file for complete search history.

(56) References Cited

U.S. PATENT DOCUMENTS 5,959,180 A * 9/1999 Moehs et al. ................. 800/298
7,439,419 B1   10/2008 McCue et al.

FOREIGN PATENT DOCUMENTS

WO   2008005474   1/2008

OTHER PUBLICATIONS

GenBank Accession No. AF249329 ([online], [retrieved on Jun. 12, 2013], retrieved from the internet <http://www.ncbi.nlm.nih.gov/nuccore/AF249329>).*

Hijmans et al., Geographic Distribution of Wild Potato Species, 88 American J of Botany No. 11, 2101-2112 (2001)).*
Communication for EP Application No. 10 81 2057 dated Jan. 17, 2013, along with Supplementary European Search Report dated Jan. 4, 2013.
Love et al., "Induced mutations for reduced tuber glycoalkaloid content in potatoes", Plant Breeding, 115:119-122 (1996).
Krits et al., "Potato steroidal glycoalkaloid levels and the expression of key isoprenoid metabolic genes", Planta; *An International Journal of Plant Biology*, 227:143-150 (2007).
G. Bartoszewski, et al., "Lycopersicon esculentum putative cytochrome P490 mRNA, complete cds.", GenBank Accession AF249329, Jul. 31, 2009, (updated [online]), http://www.ncbi.nlm.nih.gov/sviewer/viewer.fcgi?val=7582383&sat=NCBI&satkey=31762966 (Retrieved "from the internet, [retrieved on Sep. 14, 2010]."
Grzegorz Bartoszewski, et al.. "A wound inducible cytochrome P450 from tomato", Acta Physiol. Plant., 2000, pp. 269-271, vol. 22, No. 3.
H. Kato, et al., "Characterization of a wound-inducible cytochrome P450 gene (CYP72A29) that is down-regulated during crown gall tumorigenesis in potato tuber", Mol. Gen. Genomics, 2003, pp. 139-146, vol. 270.
H. Kato, et al., "Solanum tuberosum mRNA for putative cytochrome P450, complete cds.", GenBank Accession AB067685, Aug. 9, 2006, (updated [online]), http://www.ncbi.nlm.nih.gov/sviewer/viewer.fcgi?val=19911170&sat=DDBJ&satkey=5641752 (Retrieved "from the internet, [retrieved on Sep. 14, 2010]."
International Search Report of PCT/JP2010/064744 dated Sep. 28, 2010.
Kent F. McCue, et al., "The primary in vivo steroidal alkaloid glucosyltransferase from potato", Phytochem., 2006, pp. 1590-1597, vol. 67.
Kent F. McCue, et al.,"Metabolic compensation of steroidal glycoalkaloid biosynthesis in transgenic potato tubers: using reverse genetics to confirm the in vivo enzyme function of a steroidal alkaloid galactosyltransferase", Plant Science, 2005, pp. 267-273, vol. 168.
Lisa Arnqvist, et al., Reduction of Cholesterol and Glycoalkaloid Levels in Transgenic Potato Plants by Overexpression of a Type 1 Sterol Methyltransferase cDNA., Plant Physiol., Apr. 2003, pp. 1792-1799, vol. 131.

(Continued)

*Primary Examiner* — Russell Kallis
(74) *Attorney, Agent, or Firm* — Sughrue Mion, PLLC

(57) ABSTRACT

An object of the present invention is to provide DNA of a glycoalkaloid biosynthetic enzyme of a solanaceous plant (Solanaceae) such as a potato. The present invention relates to a protein having glycoalkaloid biosynthetic enzyme activity of a solanaceous plant such as a potato and a method for producing/detecting a novel organism using a gene encoding the protein.

6 Claims, 20 Drawing Sheets

(56) References Cited

OTHER PUBLICATIONS

P. C. LaRosa, et al., "Nicotiana plumbaginifolia putative cytochrome P-450 mRNA, complete cds.", Genbank Accession U35226, Aug. 9, 2006, (updated online), http://www.ncbi.nlm.nih.gov/sviewer/viewer.fcgi?val=4376202&sat=NCBI&satkey=1088680 (retrieved "from the internet, [retrieved on Sep. 14, 2010]."

\* cited by examiner

Fig. 1A

```
1st Nucleotide Sequence (SEQ ID NO:2)
  File Name      : potato C
  Sequence Size  : 1494

2nd Nucleotide Sequence (SEQ ID NO:4)
  File Name      : tomato C
  Sequence Size  : 1494

1' ATGGCAATTGCAACAGTAATTGGTGCAACAATTGGTATTTTGATAGCGATTTTTTGTGTA
       *********  ***************** ***** **********  * **** ****
    1" ATGGCAATTGTTACAGTAATTGGTGCAACGATTGGCATTTTGATAGCCCTATTTTTTGTA

61' AAATCGTTTTACACATTATGGTGGTGGCCAAAGATGATCGAAAAGAAGCTGAAGAAGGAA
       ********* **************************************************
   61" AAATCGTTTTATACATTATGGTGGTGGCCAAAGATGATCGAAAAGAAGCTGAAGAAGGAA

121' GGTATTCATGGGCTGCCCTACCAATTTCTGTTTGGAAATCTGAAAGAGATGACGAGAATG
       ********** * *** *******************************************
  121" GGTATTCATGGTCAGCCGTACCAATTTCTGTTTGGAAATCTGAAAGAGATGACGAGAATG

181' TCTAGAGAAGCAAAGAAAACACCGTTAGTAAATCATGATATCGTTCCTTGGGTTAATCCT
       ****************** *** *********** ***** ********** ******
  181" TCTAGAGAAGCAAAGAAAAAACCATTAGTAAATCACGATATTGTTCCTTGGGTGAATCCT

241' TTTATTCTTCATCTTTCTAAAACTTACGAGAGATTATTTGTGATGTGGGCTGGACCAACA
       ***********************************************************
  241" TTTATTCTTCATCTTTCTAAAACTTACGAGAGATTATTTGTGATGTGGGCTGGACCAACC

301' CCTCGGATTGTAGTATCAGATCCAAAGCTAATTAAAGAAGTGGTGAACAGACATAATGAA
       *********  **** *************** ***************************
  301" CCTCGGATTACAGTAACAGATCCAAAGCTAATAAAAGAAGTGGTGAACAGACATAATGAA

361' TTTCAGAAGCCTCAAGCCAATGCGTTCATTGACATGTTTGTTACTGGACTTGCTAGTTAC
       ***** ***************** ******** *************************
  361" TTTCAAAAGCCTCAAGCCAATGCCTTCATTGATATGTTTGTTACTGGACTTGCTAGTTAC

421' AATGGTCAAAAATGGGACCACCATAGAAAGATACTAAACCCTGCTTTTCATATAGAGAAG
       **************** *********************** ******************
  421" AATGGTCAAAAATGGGATCACCATAGAAAGATACTAAACCCGGCTTTTCATATAGAGAAG

481' ATTAAGAGGTTGTACCCAGCATTTTGTGAGTGTTGTGATGAAATGATAAATAGATGGGAG
       ************************* ********************************
  481" ATTAAGAGGTTGTACCCAGCATTTTGCGAGTGTTGTGATGAAATGATAAATAGATGGGAG
```

Fig. 1B

```
 541'  GAATTGGTTAGCAAAAGTGGAAGTTGTGAGTTGGATGTGGCAGATGAATTCCTAAATGTA
       ** ************ ************ ******* *********** *********
 541"  GACTTGGTTAGCAAAACTGGAAGTTGTGAATTGGATGTAGCAGATGAATTTCTAAATGTA

601'  GGTGGAGATGTTATATCTAGAGCTGCTTTTGGTAGCAATATTGAAGAAGGAAGGACTATT
       ***************** ******************************************
 601"  GGTGGAGATGTTATATCGAGAGCTGCTTTTGGTAGCAATATTGAAGAAGGAAGGACTATT

661'  TTCATACTTCAGAAAGAGCAGTGCGATCTTATTTTGGCTTCTCCATTTACTCTTTTCTTT
       ****************************************************** ******
 661"  TTCATACTTCAGAAAGAGCAGTGCGATCTTATTTTGGCTTCTCCATTTACTCTCTTCTTT

721'  CCCTTACTAAGATTCTTTCCAACAGCATCAAACAGAAGAGCAAGATACATCTACAAGAAA
       ************************* ****************************** ***
 721"  CCCTTACTAAGATTCTTTCCAACAGAATCAAACAGAAGAGCAAGATACATCTACAAAAAA

781'  GTGTTATCATTGATTAACGGAATAATAGAGAAGAAAAAAGACACTATGCGAAGAGGAGTC
       ************** ** ***** ************ ***** ******************
 781"  GTGTTATCATTGATCAAAGGAATCATAGAGAAGAAAGAAGACGCTATGCGAAGAGGAGTC

841'  TCACAAAGTGATGATATTTTAGGGTTACTCTTAAAAGGAGGACTATCAACCACTGAAATA
       *** ************* ***** ******************** ***************
 841"  TCAGAAAGTGATGATATATTAGGATTACTCTTAAAAGGAGGACTGTCAACCACTGAAATA

901'  ATTGAAGAATGTAAGGAATTCTATCTTGCAGGACAAGATACAACCACAGCTTTGCTCTCT
       ***********************************************************
 901"  ATTGAAGAATGTAAGGAATTCTATCTTGCAGGACAAGATACAACCACAGCTTTGCTCTCC

961'  TGGACATTGGTTGCCTTGAGTATGCACCCTGAGTGGCAAGACAAAGCTAGAAATGAAGTC
       *********** ***************** ********************** ******
 961"  TGGACATTGGTAGCCTTGAGTATGCATCCTGAGTGGCAAGACAAAGCTAGAAATGAAGTA

1021'  TTTCAAGTCCTTGGAAAAAACAAACCAAAGTTTGAGGACTTGAATCAATTAAAAATAATG
       ******** ***************************************************
1021"  TTTCAAGTACTTGGAAAAAACAAACCAAAGTTTGAGGACTTGAATCAATTAAAAATAATG

1081'  AACATGATCTTCCAAGAGGTGTTGAGATTATATCCAGCACTCACCCTTATGCGAAGCACC
       ****************************** *****************************
1081"  AACATGATCTTCCAAGAGGTGTTGAGATTATACCCAGCACTCACCCTTATGCGAAGCACC

1141'  GTAAAGAACACTAAATTGGGAGATATGACAATTCCTGCAGGAGTACAAATATTTGTGCCT
       **** ***************** ************************** *********
1141"  TCAAAGGACACTAAATTGGGAGAAATGACAATTCCTGCAGGAGTACAAATTTTTGTGCCT
```

Fig. 1C

```
1201' ATATATATAGCACATCGCGATCCCCAAGTATGGGGAGACGATGCATTGATATTCAATCCA
      ***** ************* ************************ **** ********
1201" ATATACATAGCACATCGCGACCCCCAAGTATGGGGAGACGATGCACTGATTTTCAATCCA

1261' AATAGGTTCTCAGAAGGGGTATCCAAAGCTGCAAAAGAGCCCTTGTATTTCCCCTTTGGT
      ******************************************* ************** ***
1261" AATAGGTTCTCAGAAGGGGTATCCAAAGCTGCAAAAGAGCCATTGTATTTCCCCTTCGGT

1321' TGGGGTCCTCGAATGTGCATTGGTAATAACTTTGGCATGGCAGAAGCCAAGCTCGTTTTA
      ************************************ *********** ************
1321" TGGGGTCCTCGAATGTGCATTGGTAATAACTTTGGAATGGCAGAAGCAAAGCTCGTTTTA

1381' TCTCAAATTCTGCAGCGTTTTTGGTTTAAGCTCTCTCCTTCCTATGTTCATGCCCCTCAG
      ************** * ******** *********************************
1381" TCTCAAATTCTGCAGAGGTTTTGGTTCAAGCTCTCTCCTTCCTATGTTCATGCCCCTCAG

1441' GCAATACTCGTTATGAAGCCTCAGTATGGTGCTCAGATAATCCTCAACAAGCTT
      *****************************************************
1441" GCAATACTCGTTATGAAGCCTCAGTATGGTGCTCAGATAATCCTCAACAAGCTC
```

Fig. 3
A)
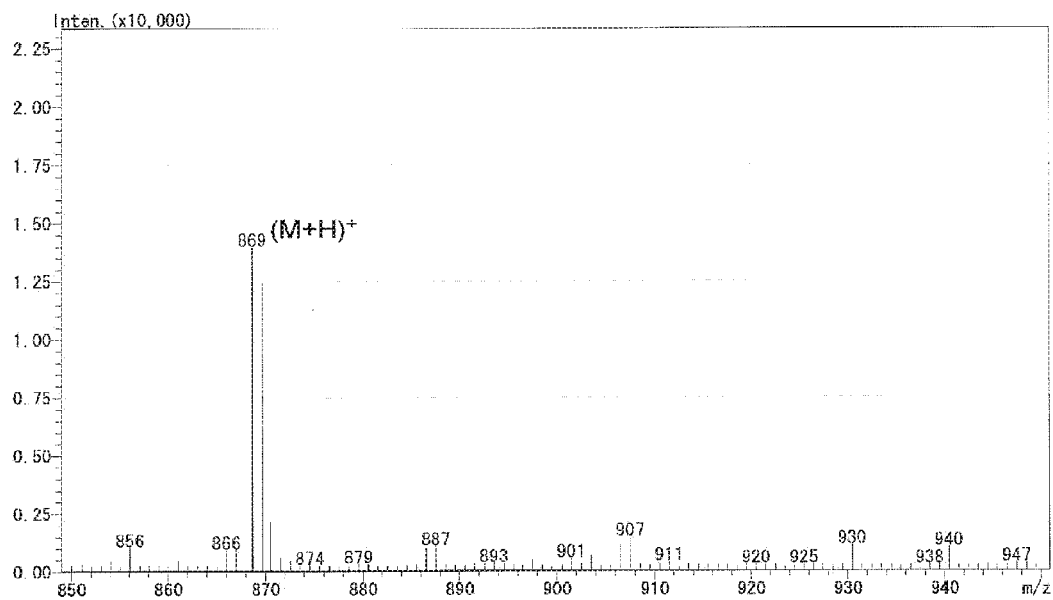
B)
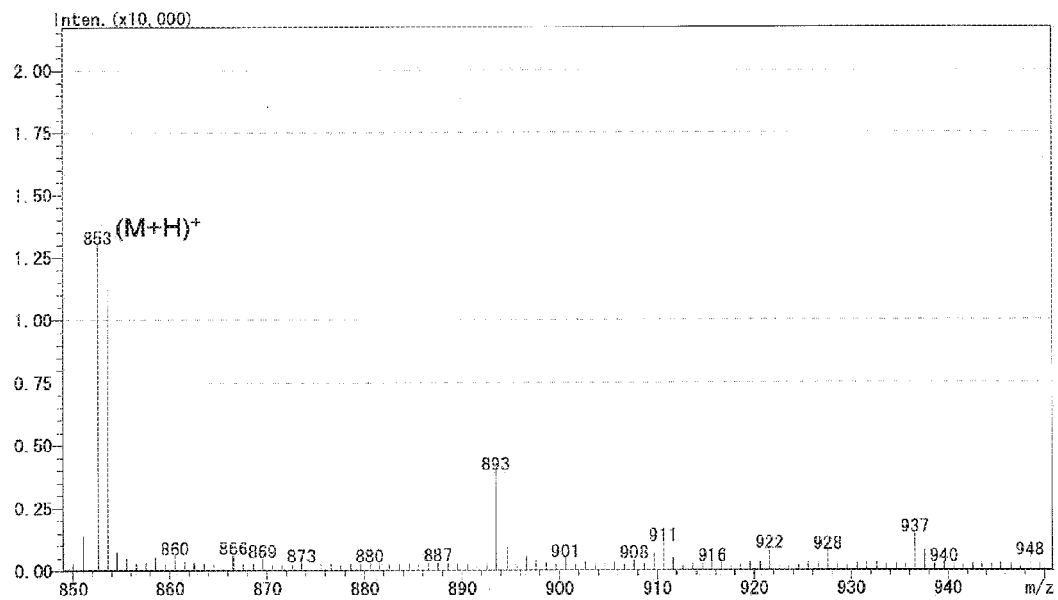

Fig. 4
A)
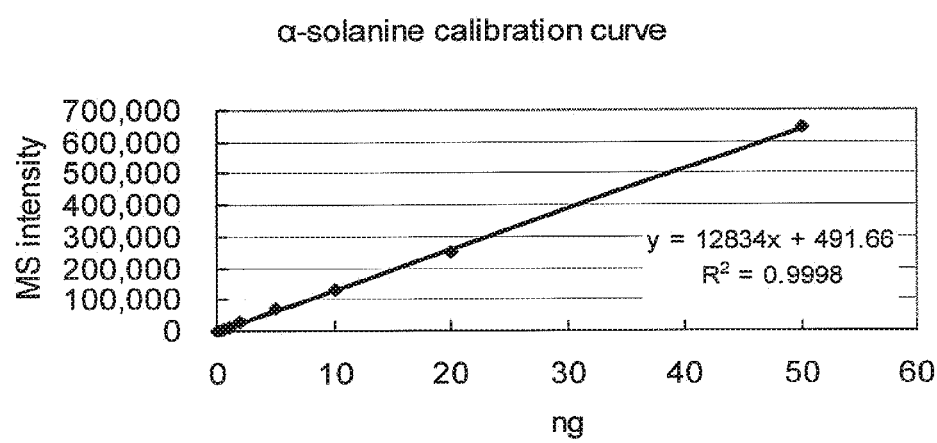
α-solanine calibration curve
B)
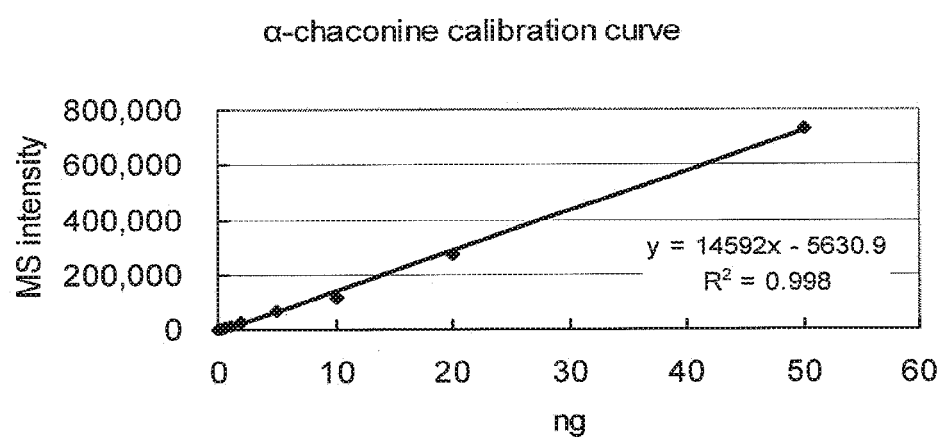
α-chaconine calibration curve
C)
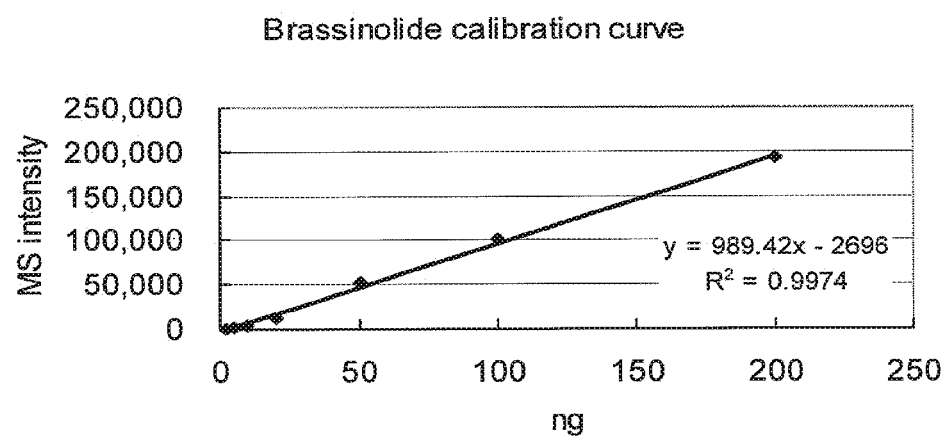
Brassinolide calibration curve 1: Non-transformant
2: Non-transformant
3: pKT226 transformant (#20)
4: pKT226 transformant (#35)
5: pKT226 transformant (#45)
6: pKT226 transformant (#67)

Fig. 11A

1st Nucleotide Sequence (SEQ ID NO:19)
  File Name      : potato D
  Sequence Size  : 1551

2nd Nucleotide Sequence (SEQ ID NO:21)
  File Name      : tomato D
  Sequence Size  : 1548

```
   1' ATGGGTATTGCAGTTTTCATTGCTTTGGCCGTATGTTTGCCTTTCAGTTTTTGGTGCCTA
      **** ******* ******* ********* *** *** ******* *************
   1" ATGGCTATTGCAATTTTCATAGCTTTGGCCATATTTTTTCCTTTCACTTTTTGGTGCCTA

61' AAATTGCTCTACTTTGTATGGTGGCGTCCCAAAACAGTAGAAAATGAACTGCGGCAGCAA
      ****************************** *********************** ** ***
  61" AAATTGCTCTACTTTGTATGGTGGCGTCCGAAAACAGTAGAAAATGAACTGCGTCATCAA

121' GGAATATATGGGCGTCCCTATAGATTTCTATTTGGAAATCTAAAGGAGATGATAGAGATG
      *****  *************************************** ***************
 121" GGAATCTATGGGCGTCCCTATAGATTTCTATTTGGAAATCTAAAAGAGATGATAGAGATG

181' AATAAAATAGCCAAGTCTAAACCCATGCCATTGCACCACGATTTCACACCTCGACTTAAT
      **  ********** *********************************************
 181" AACAAAATAGCCAAATCTAAACCCATGCCATTGCACCACGATTTCACACCTCGACTTAAT

241' CCATTGTTCTATGAACTGGCCACCACTTACAAGAAACTTTACTTGTTTTGGCTAGGACCG
      ***************** ** ***************************************
 241" CCATTGTTCTATGAACTCGCTACCACTTACAAGAAACTTTACTTGTTTTGGCTAGGACCC

301' ATACCTCGATTAACCATTTTGGATCCCAAGTTAATTAAGGAAGTACTGTCAAACAAATCG
      ** ******************************  *********************
 301" ATCCCTCGATTAACCATTTTGGATCCCAAGTTAATAAAGGAAGTACTGTCAAACAAATCT

361' GGTGAGTTCAGAAAACCAAACATCAGCGCTTTCCTGAAGCTATTTGTAACGGGGCTGGGG
      ****************** ***** ***** ****************** ***** ***
 361" GGTGAGTTCAGAAAACCAAAAATCAGTGCTTTTCTGAAGCTATTTGTAACAGGGCTAGGG

421' ACTTACGATGGTGAAAAATGGGCGAAACACAGAAAAATTCTTAATCCGGCTTTCCACATG
      ********** ********** ***** ******************* *********
 421" ACTTACGATGGGGAAAAATGGGCCAAACATCGAAAAATTCTTAATCCGGCATTCCACATG

481' GAAAAATTGAAGGTGATGTTGGGATTATTTGTTAACTGTACCGATGACATGATAAGCAGA
      ***************** ************** * ** ** ******************
 481" GAAAAATTGAAGGTGATGCTGGGATTATTTGTTGAATGCACGGATGACATGATAAGCAGA
```

Fig. 11B

```
541'  TGGGACAAGCTAACTGGTTCAACGGGTGGTTCTTGTGAAGTAGATATTTCTCAAGAATTT
      ***** ******** **********   ********* * *******************
541"  TGGGATAAGCTAACGGGTTCAACGGG---TTCTTGTGAATTGGATATTTCTCAAGAATTT

601'  CATAATTTAACTGGAGATATGCTATCGAAAGCAGCCTTCGGTAGCAATTTTGAAGAAGGG
      ****************************** *****************************
598"  CATAATTTAACTGGAGATATGCTATCGAAAGCAGCTTTCGGTAGCAATTTTGAAGAAGGG

661'  AAGTTGGTATTTTCACTTCTGAGAGAGCAATGTGAACTAATTTTCACTGCAAAGCTTGCT
      ** *********************************************************
658"  AAATTGGTATTTTCACTTCTGAGAGAGCAATGTGAACTAATTTTCACTGCAAAGCTTGCT

721'  ATTAATGTCTTCCCATGGTTAAGGTTTGTGCCAACGAAAACTAATAGGAGAAGATTGTAC
      ************************************************************
718"  ATTAATGTCTTCCCATGGTTAAGGTTTGTGCCAACGAAAACTAATAGGAGAAGATTGTAC

781'  ATCTATAACACAGTTCGTAGTTCGCTAAAAGCAATAATTGAGAAACGAGAGAAAGAGGTA
      ************************ ***** **** ************************
778"  ATCTATAACACAGTTCGTAGTTCGTTAAAATCAATCATTGAGAAACGAGAGAAAGAGGTA

841'  CAATCTGGAAAATCACACAATGAAGATCTGTTGGGTTTGCTAATGAAATCTAATCAGGAA
      ******************** ******** ********* * ******************
838"  CAATCTGGAAAATCACACAACGAAGATCTATTGGGTTTGTTGATGAAATCTAATCAGGAA

901'  GAACAGCAAGGGAATAAGAACTCGAACAAAGGAATGAGTACAGAGGATATGATAGAAGAG
      ****************************** *****************************
898"  GAACAGCAAGGGAATAAGAACTCGAATAAAGGAATGAGTACAGAGGATATGATAGAAGAG

961'  TGCAACTCTTTCTATTTTGCTGGTCAAGAGACTACTGCAACTTTGTTAACATGGACTGCA
      ** *********** *********************************************
958"  TGTAACTCTTTCTACTTTGCTGGTCAAGAGACTACTGCAACTTTGTTAACATGGACTGCA

1021' ATTGTCTTGACTATGCATCCAGATTGGCAAGAGAAAGCCAGGAAAGAAGTTCTTGAAGTC
      ***** ******************************** ************** *****
1018" ATTGTGTTGACTATGCATCCAGATTGGCAAGAGAAAGCTAGGAAAGAAGTTCTTCAAGTC

1081' ATTGGAAAAGATGAGCCTAAGTTTGATCAACTCAACCATCTAAAGATTGTAACTATGATC
      ************* ****************************** ***********  **
1078" ATTGGAAAAGATGAACCTAAGTTTGATCAACTCAACCACCTAAAGATTGTAACAATGATT

1141' TTGCACGAGGTTCTGAGGTTATATCCATCAGGTTCTCTTGTTAGAGAAACAAACAAAAAG
      ***************** ****************** ***********************
1138" TTGCACGAGGTTCTGAGGCTCTATCCATCAGGTTCTCTCGTTAGAGAAACAAACAAAAAA
```

Fig. 11C

```
1201' ACAAAGCTTGGAGAGTATACAATCCCAGCAGGTGCGCAACTTTTAGTTCCTCTACAAACA
      ******* ****  ****************************** ************
1198" ACAAAGCTCGGAGGGTATACAATCCCAGCAGGTGCGCAACTTTTAGTGCCTCTACAAACA

1261' ATCCATCGCGATACAGAGGCATGGGGAGAAGATGCTCTAATTTTCAATCCAGAAAGGTTT
      ** *****  ****************** *******  ************************
1258" ATTCATCGGGATACAGAGGCATGGGGTGAAGATGCATTAATTTTCAATCCAGAAAGGTTT

1321' TCAGAAGGGGTATCAAAAGCATCAAAGGACCTGATGTACTTTCCGTTTGGTTGGGGTTCT
      ******************************************  ** ***************
1318" TCAGAAGGGGTATCAAAAGCATCAAAGGACCTGATGTACTTCCCATTTGGTTGGGGTTCT

1381' CGGATATGCCTTGGAATGAATGTTTCCATGATTCAAGGGAAGCTTGTTTTGGCTAAAATC
      ************************** *********************************
1378" CGGATATGCCTTGGAATGAATGTTTCGATGATTCAAGGGAAGCTTGTTTTGGCTAAAATC

1441' TTACAGAACTACTCCTTTGAGCTTTCCCCCTCCTATGCTCATGGTCCAACCATGCCAGCT
      ************** *************  *********************  *********
1438" TTACAGAACTACTCATTTGAGCTTTCCCCATCCTATGCTCATGGTCCAACAATGCCAGCT

1501' CTTGTTCTACAACCACAATATGGTGCTCCTATGATCCTTCGAAAGCTATCA
      ********************************    **********
1498" CTTGTTCTACAACCACAATATGGTGCTCCTATGATTGTTCGAAAGCTAGAA
```

1: Non-transformant
2: Non-transformant
3: pKT227 transformant (#9)
4: pKT227 transformant (#10)
5: pKT227 transformant (#22)
6: pKT227 transformant (#25)
7: pKT227 transformant (#28)
8: pKT227 transformant (#45)
9: pKT227 transformant (#59)
10: pKT227 transformant (#61)

US 9,598,699 B2

PROTEIN HAVING GLYCOALKALOID BIOSYNTHETIC ENZYME ACTIVITY AND GENE ENCODING THE SAME

CROSS REFERENCE TO RELATED APPLICATIONS

This application is a National Stage of International Application No. PCT/JP2010/064744 filed Aug. 30, 2010, claiming priority based on Japanese Patent Application No. 2009-198889, filed Aug. 28, 2009 and Japanese Patent Application No. 2010-108445, filed May 10, 2010, the contents of all of which are incorporated herein by reference in their entirety.

TECHNICAL FIELD

The present invention relates to a method for producing a glycoalkaloid compound characteristic of a solanaceous plant such as a potato, a glycoalkaloid biosynthetic enzyme, DNA encoding the glycoalkaloid biosynthetic enzyme, a method for breeding or selecting a novel solanaceous plant such as a potato using the DNA, and a solanaceous plant such as a potato that produces no glycoalkaloid.

BACKGROUND ART

Glycoalkaloids are members of plant-derived compounds and are said to be steroidal alkaloids. It has been reported that the glycoalkaloid structure has an N atom and is an isoprenoid having 27 carbon chains, and there are 422 compounds of glycoalkaloids from plants belonging to the genus *Solanum* (Non-Patent Literature 1: Chapter 7.8). In addition to solanaceous plants belonging to the genus *Solanum*, plants belonging to the family Liliaceae are known to contain glycoalkaloids. Important glycoalkaloids are chaconine and solanine from potatoes (*Solanum tuberosum*) belonging to the genus *Solanum* of the family Solanaceae and tomatine from tomatoes (*Solanum lycopersicum*).

The potato is the world's forth largest crop produced, following maize, rice, and wheat. It is well known that buds sprouting from the tubers and aerial parts of the potato contain chaconine and solanine, which are toxic substances. Chaconine and solanine cause toxic symptoms such as abdominal pain, dizziness, and mild disturbances of consciousness. Also, chaconine and solanine are likely to accumulate in tubers as a result of damage or exposure to sunlight. Therefore, there is the risk of accidental poisoning as a result of a failure in tuber management. Accidental glycoalkaloid poisoning sometimes occurs. In a recent case, accidental glycoalkaloid poisoning occurred in an elementary school in Nara city in Japan on Jul. 16, 2009 (reported by Asahi.com). The glycoalkaloid levels in potato tubers are controlled at 20 mg/100 g or lower by, for example, storing the tubers in dark places. Thus, in general, potato tubers are safe food products. However, in consideration of the risk of accidental poisoning described above, reduction of potato glycoalkaloid content is a key issue for those involved in breeding, production, storage, transportation, distribution, or purchasing in the potato-related industry. However, reduction of potato glycoalkaloid content has not been achieved thus far. This is because there is no wild-type potato line free from glycoalkaloids, the glycoalkaloid biosynthesis pathway has not been elucidated (Non-Patent Literature 1 (FIGS. 7.24 A and B) and Non-Patent Literature 2), and there has been little progress in identification of genes involved in the biosynthesis pathway.

It is known that glycoalkaloids have medicinal properties such as anticancer activity, liver-protecting effects, antispasmodic effects, immune-system-promoting effects, antifungal effects, antiprotozoal effects, and molluscicide activity, in addition to poisonous properties such as anticholinesterase activity and membrane disruption effects (Non-Patent Literature 1). It has been reported that esculeoside A, which is a glycoalkaloid metabolite, shows anti-arteriosclerotic effects in tomatoes (Non-Patent Literature 3). However, since the biosynthesis pathway has not been elucidated, there has been substantially no advance in research and development to suppress or efficiently produce metabolites.

In recent years, there have been some reports on genes involved in the glycosylation after transfer of a sugar to aglycone (Non-Patent Literature 4-6). Non-Patent Literature 4 reports that a UDP-galactosyltransferase gene is involved in the pathway of formation of γ-solanine from solanidine (aglycone), and it also reports a strain in which the gene is suppressed. However, suppression of chaconine has been never achieved (Non-Patent Literature 4 (FIG. 2)). Non-Patent Literature 4 reports that a UDP-glucosyltransferase gene is involved in the pathway of formation of γ-chaconine from solanidine, and it also reports a strain in which the gene is suppressed. However, suppression of chaconine and solanine has been substantially impossible (Non-Patent Literature 5 (FIG. 5)). Non-Patent Literature 6 reports a rhamnosyltransferase gene involved in the pathway of formation of α-chaconine from β-chaconine and the pathway of formation of α-solanine from β-solanine. In this case, β-isomer or γ-isomer increases while α-isomer decreases. Thus, it is understood that it has been very difficult to control total glycoalkaloid content, even though it has become possible to change the molecular species of glycoalkaloid by suppressing the glycosylation.

There is a report of an attempt to reduce glycoalkaloid through overexpression of genes involved in biosynthesis of plant sterols and plant hormones (Non-Patent Literature 7). However, in such case, it was merely possible to reduce the glycoalkaloid content up to almost half the initial amount (Non-Patent Literature 7 (FIG. 5)).

CITATION LIST

Non Patent Literature

Non-Patent Literature 1: Eich, Soloanaceae and Convolvulaceae: Secondary Metabolite (2008), Springer
Non-Patent Literature 2: Ginzberg et al., Potato Research (2009) 52: 1-15
Non-Patent Literature 3: Fujiwara et al., Abstracts of the Annual Meeting of Japan Society for Bioscience, Biotechnology, and Agrochemistry 2008, 2B07, p. 22
Non-Patent Literature 4: McCue et al., Plant Sci. (2005) 168: 267-273
Non-Patent Literature 5: McCue et al., Phytochemistry (2006) 67: 1590-1597
Non-Patent Literature 6: McCue et al., Phytochemistry (1998) 68: 327-334
Non-Patent Literature 7: Arnqvist et al., Plant Physiol. (2003) 131: 1792-1799

SUMMARY OF INVENTION

Technical Problem

An object of the present invention is to provide a method for producing a glycoalkaloid compound characteristic of a solanaceous plant such as a potato, a glycoalkaloid biosynthetic enzyme, DNA encoding the glycoalkaloid biosynthetic enzyme, a method for breeding or selecting a novel solanaceous plant such as a potato using the DNA, and a solanaceous plant such as a potato that produces no glycoalkaloid.

Solution to Problem

The present inventors conducted intensive studies in order to achieve the above object. First, the present inventors focused on the process prior to aglycone formation. Then, the present inventors searched in silico for candidate genes involved in the biosynthesis pathway and suppressed expression of endogenous candidate genes by causing expression of parts of the candidate genes to induce RNAi. As a result, the present inventors succeeded in obtaining a potato having remarkably reduced glycoalkaloid content from the transformants and identifying the glycoalkaloid biosynthetic enzyme gene. In addition, the present inventors demonstrated that it is possible to obtain a solanaceous plant such as a potato lacking glycoalkaloids by selecting a plant in which the expression of the above gene is suppressed. Further, the present inventors demonstrated that it becomes possible to produce a novel glycoalkaloid compound by expression of the gene, and it also becomes possible to analyze polymorphisms by comparing the genomic sequence of the gene with the genomic sequences of different solanaceous plants such as potatoes, thereby making it possible to establish a newly bred solanaceous plant variety such as a potato variety. This has led to the completion of the present invention. Similarly, the present inventors succeeded in producing a tomato having reduced glycoalkaloid content by suppressing the endogenous gene in the above manner.

Specifically, the present invention encompasses the following inventions.

[1] A protein, which is the following (a) or (b):
(a) a protein comprising the amino acid sequence shown in SEQ ID NO: 1 or 18; or
(b) a protein having glycoalkaloid biosynthetic enzyme activity and comprising an amino acid sequence that has a deletion, substitution, insertion, or addition of one or several amino acids with respect to the amino acid sequence shown in SEQ ID NO: 1 or 18.

[2] A gene, which comprises DNA selected from among the following (c) to (f):
(c) DNA consisting of the nucleotide sequence shown in SEQ ID NO: 2 or 19;
(d) DNA that hybridizes under stringent conditions to DNA consisting of a nucleotide sequence complementary to DNA consisting of the nucleotide sequence shown in SEQ ID NO: 2 or 19 and encodes a protein having glycoalkaloid biosynthetic enzyme activity;
(e) DNA that consists of a nucleotide sequence having 80% or more sequence identity to the nucleotide sequence shown in SEQ ID NO: 2 or 19 and encodes a protein having glycoalkaloid biosynthetic enzyme activity; or
(f) DNA consisting of a degenerate isomer of the nucleotide sequence shown in SEQ ID NO: 2 or 19.

[3] A protein, which is the following (g) or (h):
(g) a protein comprising the amino acid sequence shown in SEQ ID NO: 3 or 20; or
(h) a protein having glycoalkaloid biosynthetic enzyme activity and comprising an amino acid sequence that has a deletion, substitution, insertion, or addition of one or several amino acids with respect to the amino acid sequence shown in SEQ ID NO: 3 or 20.

[4] A gene, which comprises DNA selected from among the following (i) to (l):
(i) DNA consisting of the nucleotide sequence shown in SEQ ID NO: 4 or 21;
(j) DNA that hybridizes under stringent conditions to DNA consisting of a nucleotide sequence complementary to DNA consisting of the nucleotide sequence shown in SEQ ID NO: 4 or 21 and encodes a protein having glycoalkaloid biosynthetic enzyme activity;
(k) DNA that consists of a nucleotide sequence having 80% or more sequence identity to the nucleotide sequence shown in SEQ ID NO: 4 or 21 and encodes a protein having glycoalkaloid biosynthetic enzyme activity; or
(l) DNA consisting of a degenerate isomer of the nucleotide sequence shown in SEQ ID NO: 4 or 21.

[5] A recombinant vector, which comprises the gene according to [2] or [4].
[6] A transformant, to which the recombinant vector according to [5] is introduced.
[7] The transformant according to [6], which is a plant.
[8] A method for detecting the existence of a mutation and/or polymorphism of a gene encoding a glycoalkaloid biosynthetic enzyme in a plant, which comprises:
(i) a step of isolating a nucleic acid in the form of genomic DNA or RNA from a plant;
(ii) a step of synthesizing cDNA via reverse transcription when the nucleic acid in (i) is RNA;
(iii) a step of amplifying a gene fragment comprising the nucleotide sequence shown in SEQ ID NO: 2, 4, or 5 or the nucleotide sequence shown in SEQ ID NO: 19, 21, or 22 from DNA obtained in step (i) or (ii); and
(iv) a step of determining the existence of a mutation and/or polymorphism in the DNA.
[9] The method according to [8], wherein the plant is a plant belonging to the family Solanaceae.
[10] A method for selecting a plant having a mutation and/or polymorphism, which comprises detecting a mutation and/or polymorphism of a gene encoding a glycoalkaloid biosynthetic enzyme by the method according to [8] or [9].
[11] A plant having a mutation and/or a polymorphism in a gene encoding a glycoalkaloid biosynthetic enzyme, which is selected by the method according to [9].
[12] The plant according to [11], which is a plant belongs to the family Solanaceae.
[13] A method for selecting the plant according to [8] or [9], which comprises selecting a plant in which the ability to express a gene encoding a glycoalkaloid biosynthetic enzyme or the activity of a glycoalkaloid biosynthetic enzyme encoded by the gene is altered from that in an existing variety.
[14] A plant selected by the method according to [13], in which the ability to express a gene encoding a glycoalkaloid biosynthetic enzyme or the activity of a glycoalkaloid biosynthetic enzyme encoded by the gene is altered from that in an existing variety.
[15] The plant according to [14], which is a plant belonging to the family Solanaceae.

This description includes part or all of the contents as disclosed in the descriptions and/or drawings of Japanese Patent Application Nos. 2009-198889 and 2010-108445, which are priority documents of the present application.

Advantageous Effects of Invention

According to the present invention, it is possible to regulate expression of the activity of a protein having glycoalkaloid compound biosynthesis activity characteristic of a solanaceous plant such as a potato and that of a gene encoding the protein. Specifically, a method for producing a plant in which activity of such gene is regulated and a solanaceous plant such as a potato that produces no glycoalkaloid are provided. The present invention enables breeding of a solanaceous plant such as a potato having the feature of containing a glycoalkaloid compound. The use of the enzyme of the present invention allows the mass production of glycoalkaloid compounds that exhibit a variety of useful physiological activities at low prices.

BRIEF DESCRIPTION OF DRAWINGS

FIG. 1A shows results of analysis of biosynthesis gene C homology between a potato (SEQ ID NO: 2; the top sequence in the pairwise alignment) and a tomato (SEQ ID NO: 4; the bottom sequence in the pairwise alignment) using the GENETYX DNA analysis software (Genetyx Corporation). The overall results indicate very high homology.

FIG. 1B shows results of analysis of biosynthesis gene C homology between a potato and a tomato using the GENE-TYX DNA analysis software (Genetyx Corporation) (continued from FIG. 1A).

FIG. 1C shows results of analysis of biosynthesis gene C homology between a potato and a tomato using the GENE-TYX DNA analysis software (Genetyx Corporation) (continued from FIG. 1B).

FIG. 2 shows the inner construct between the right border (RB) and the left border (LB) and restriction enzyme sites in T-DNA which is a gene fragment to be introduced.

FIG. 3 shows an MS spectrum for the protonated parent ion peak (M+H)$^+$ for α-solanine (A) and an MS spectrum for the protonated parent ion peak (M+H)$^+$ for α-chaconine (B).

FIG. 4 shows a calibration curve (LC-MS quantitative determination analysis system) for α-solanine (A), a calibration curve (LC-MS quantitative determination analysis system) for α-chaconine (B), and a calibration curve (LC-MS quantitative determination analysis system) for brassinolide (C).

FIG. 11A shows results of analysis of biosynthesis gene D homology between a potato (SEQ ID NO: 19; the top sequence in the pairwise alignment) and a tomato (SEQ ID NO: 21; the bottom sequence in the pairwise alignment) using the GENETYX DNA analysis software (Genetyx Corporation). The overall results indicate very high homology.

FIG. 11B shows results of analysis of biosynthesis gene D homology between a potato and a tomato using the GENE-TYX DNA analysis software (Genetyx Corporation) (continued from FIG. 11A).

FIG. 11C shows results of analysis of biosynthesis gene D homology between a potato and a tomato using the GENE-TYX DNA analysis software (Genetyx Corporation) (continued from FIG. 11B).

FIG. 12 shows the inner construct between the right border (RB) and the left border (LB) and restriction enzyme sites in T-DNA which is a gene fragment to be introduced.

DESCRIPTION OF EMBODIMENTS

Figure 2:
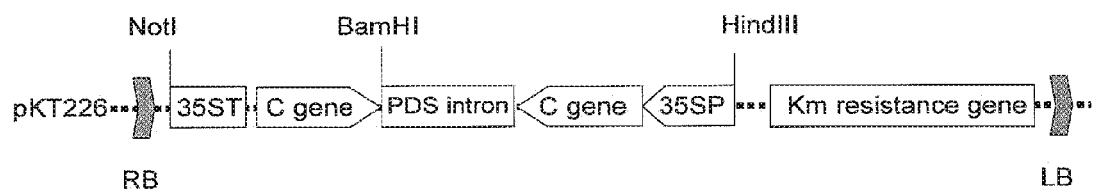
FIG. 2 shows a vector construct used for suppression of a candidate C gene.

The present invention is described in detail below.
1. A novel Glycoalkaloid Biosynthetic Enzyme The protein/enzyme of the present invention is a glycoalkaloid biosynthetic enzyme contained in a solanaceous plant (Solanaceae) such as a potato. Plants such as potatoes belonging to the family Solanaceae include potatoes (*Solanum tuberosum*), tomatoes (*Solanum lycopersicum*), eggplants (*Solanum melongena*), and capsicums (*Capsicum annum*). In addition, the enzyme of the present invention is a membrane-bound cytochrome P450 monooxidase. Examples of glycoalkaloids obtained using the enzyme of the present invention include a glycoalkaloid synthesized by a solanaceous plant such as a potato. Examples thereof include glycoalkaloids such as chaconine and solanine contained in potatoes and glycoalkaloids such as tomatine contained in tomatoes.

Examples of a preferable steroid compound that can be used as a substrate for the glycoalkaloid biosynthetic enzyme of the present invention include cholesterols. Examples of cholesterols include cholesterol, sitosterol, campesterol, stigmasterol, and brassicasterol. The glycoalkaloid biosynthetic enzyme of the present invention is a hydroxylation enzyme that transfers a hydroxyl group to any of the above cholesterols.

The full-length amino acid sequence of the enzyme of the present invention is shown in SEQ ID NO: 1 or 3 (gene C) or SEQ ID NO: 18 or 20 (gene D). Further, the protein of the present invention includes a protein having glycoalkaloid biosynthetic enzyme activity and comprising an amino acid sequence substantially identical to the amino acid sequence shown in SEQ ID NO: 1 or 3 or the amino acid sequence shown in SEQ ID NO: 18 or 20. Here, an example of such a substantially identical amino acid sequence is an amino acid sequence that has a deletion, substitution, insertion, and/or addition of one or several amino acids (1 to 10 amino acids, preferably 1 to 7 amino acids, more preferably 1 to 5 amino acids, further preferably 1 to 3 amino acids, and even further preferably 1 amino acid or 2 amino acids) with respect to the above amino acid sequence. Alternatively, it is an amino acid sequence having at least 85% or more, preferably 90% or more, more preferably 95% or more, and particularly preferably 97% or more sequence identity to the above amino acid sequence when the sequence identity is calculated using, for example, BLAST (the Basic Local Alignment Search Tool at the National Center for Biological Information) (based on, for example, default (i.e., initial setting) parameters).

The glycoalkaloid biosynthetic enzyme of the present invention includes a natural glycoalkaloid biosynthetic enzyme isolated from a plant and a recombinant glycoalkaloid biosynthetic enzyme produced by a gene engineering technique.

2. A Gene Encoding a Glycoalkaloid Biosynthetic Enzyme

The gene of the present invention is a gene encoding a glycoalkaloid biosynthetic enzyme having activity of binding a hydroxyl group to a steroid compound, and it also encodes a protein having the above glycoalkaloid biosynthetic enzyme activity.

The DNA nucleotide sequence of the gene of the present invention is the nucleotide sequence shown in SEQ ID NO: 2 or 4 or the nucleotide sequence shown in SEQ ID NO: 19 or 21. Further, the DNA of the present invention includes: DNA that hybridizes under stringent conditions to DNA comprising a nucleotide sequence complementary to the nucleotide sequence shown in SEQ ID NO: 2 or 4 or the nucleotide sequence shown in SEQ ID NO: 19 or 21; DNA having at least 85% or more, preferably 90% or more, more preferably 95% or more, and particularly preferably 97% or more sequence identity to the nucleotide sequence shown in SEQ ID NO: 2 or 4 or the nucleotide sequence shown in SEQ ID NO: 19 or 21 when the sequence identity is calculated using, for example, BLAST (the Basic Local Alignment Search Tool at the National Center for Biological Information) (based on, for example, default (i.e., initial setting) parameters); and DNA that encodes a protein comprising an amino acid sequence that has a deletion, substitution, insertion, and/or addition of one or several amino acids (1 to 10 amino acids, preferably 1 to 7 amino acids, preferably 1 to 5 amino acids, more preferably 1 to 3 amino acids, and further preferably 1 amino acid or 2 amino acids) with respect to the amino acid sequence of a protein encoded by the above DNA and comprises a protein having glycoalkaloid biosynthetic enzyme activity. Here, the term "stringent conditions" refers to, for example, conditions comprising "1×SSC, 0.1% SDS, 37° C." More stringent conditions comprise "0.5×SSC, 0.1% SDS, 42° C." Further stringent conditions comprise "0.2×SSC, 0.1% SDS, 65° C." In addition, the gene of the present invention includes DNA comprising a degenerate isomer of the nucleotide sequence shown in SEQ ID NO: 3 or 4.

3. Recombinant Vectors

The vector of the present invention is a recombinant vector into which DNA shown in SEQ ID NO: 2 or 4 or DNA shown in SEQ ID NO: 19 or 21 has been inserted. As such vector, a wide range of known vectors for yeasts, plant cells, insect cells, and the like can be used. Examples of known vectors for yeasts include pDR196, pYES-DEST 52, Yip5, Yrp17, and Yep24. Examples of known vectors for plant cells include the pGWB vector, pBiE12-GUS, pIG121-Hm, pBI121, pBiHyg-HSE, pB119, pBI101, pGV3850, and pABH-Hm1. Examples of known vectors for insect cells include pBM030, pBM034, and pBK283. A vector used in the present invention incorporates components involved in gene expression or suppression such as a promoter, a terminator, and an enhancer. If necessary, the vector contains selection markers (e.g., a drug-resistant gene, an antibiotic-resistant gene, and a reporter gene). It is preferable for the components involved in gene expression or suppression to be incorporated into a recombinant vector in a manner such that they can independently function in accordance with their properties. A person skilled in the art can adequately carry out procedures of such incorporation.

4. Transformants

The transformant of the present invention is a transformant having the recombinant vector of the present invention. Such transformant can be obtained by introducing a recombinant vector into which a gene encoding an enzyme has been inserted into a host in a manner such that the gene of interest is expressed therein. A host appropriate for a vector can be used. Examples of hosts include yeasts, plant cells, insect cells (e.g., Sf9), and plant viruses. Preferable examples thereof include yeasts, plant cells, and plant viruses. A method for introducing a recombinant vector is not particularly limited as long as it is a method for introducing DNA into a microorganism. Examples of such method include a method using calcium ions (Cohen, S. N. et al.: Proc. Natl. Acad. Sci., USA, 69:2110 (1972)), an electroporation method, and a tri-parental mating method. In addition, an example of a method for producing a transformed plant is a method using, as a vector, a virus, a Ti plasmid or Ri plasmid of *Agrobacterium*, or the like. Examples of host plants include monocotyledonous plants such as rice, barley, and maize and dicotyledonous plants such as soybeans, rapeseeds, tomatoes, and potatoes. A transformed plant can be obtained through regeneration using plant cells transformed with the gene of the present invention. Regeneration of a plant from plant cells can be carried out by a known method.

5. A Method for Producing a Glycoalkaloid Biosynthetic Enzyme and a Method for Producing a Glycoalkaloid Compound The glycoalkaloid biosynthetic enzyme of the present invention is a membrane-bound cytochrome P450 monooxidase, and it can be collected from a general plant (e.g., Collu et al., 2001, FEBS Lett. 508:215-220). In addition, the glycoalkaloid biosynthetic enzyme of the present invention can be produced via, for example, mass production using an expression system for microorganisms (e.g., yeast) or insect cells transformed with the gene of the present invention. An example of the use of insect cells has been reported by Morikawa et al. (2006, Plant Cell 18: 1008-1022).

The glycoalkaloid biosynthetic enzyme of the present invention can be expressed in the form of a highly active protein using such system. Therefore, a glycoalkaloid compound can be produced with the addition of the substrate of the glycoalkaloid biosynthetic enzyme to a transformed yeast or insect cell culture liquid. For example, a hydroxylated cholesterol can be efficiently mass-produced by administering, as a substrate, a cholesterol to a transformed yeast culture liquid. It has been reported that yeast has a pathway of biosynthesis of DMAPP in cytosol (mevalonate pathway), and a precursor or substrate can be produced by introducing a mevalonate pathway into *Escherichia coli* (Harada & Misawa, 2009 Aug. 12. Epub Appl Microbiol Biotechnol.). It becomes possible to simultaneously express a membrane-bound cytochrome P450 monooxidase and a different gene so as to produce a glycoalkaloid in the above manner. For example, a metabolite was obtained by causing the expression of a membrane-bound cytochrome P450 monooxidase using *Escherichia coli* (reported by Chang et al. (2007 Nat. Chem. Biol. 3:274-277)) and yeast (reported by Seki et al. (2008 PNAS 105:14204-14209)). The combined use of techniques used in the above cases allows production of a glycoalkaloid compound.

6. Selection of Gene Mutation, Polymorphism, and Gene Expression Mutation

According to the present invention, a method for detecting the existence of a glycoalkaloid biosynthetic enzyme gene mutation, a polymorphism such as a single nucleotide polymorphism (SNP), or a gene expression mutation in a plant is provided. A mutant may be obtained via radiation, chemical treatment, UV irradiation, or natural mutation.

The above method comprises: a step of isolating genomic DNA or RNA from a mutant plant, a plant of a different variety or breeding line and carrying out reverse transcription for cDNA synthesis if RNA is isolated; a step of amplifying a gene fragment containing a glycoalkaloid biosynthetic enzyme gene from DNA using a DNA amplification technique; and a step of determining the existence of a mutation in the DNA. A commercially available kit (e.g., DNeasy or RNeasy (QIAGEN)) can be used in a method for extracting DNA or RNA. Also, a commercially available kit (e.g., a SuperScript First-Strand System (Invitrogen)) can be used for cDNA synthesis. For example, techniques such as the so-called PCR and LAMP techniques can be used as methods for amplifying a gene fragment using a DNA amplification technique. Such techniques are included in a group of techniques involving the use of a polymerase so as to amplify (i.e., to increase the number of copies of) a specific DNA sequence in a continuous polymerase reaction. Such reaction can be employed instead of cloning. In such case, nucleic acid sequence information is the only requirement for the reaction. In order to carry out DNA amplification, primers complementary to a DNA sequence to be amplified are designed. Then, the primers are produced via automatic DNA synthesis. DNA amplification methods are known in the art, and thus a person skilled in the art can readily carry out such a method based on teachings and instructions described herein. Some PCR methods (and related techniques) are described in, for example, U.S. Pat. Nos. 4,683,195, 4,683,202, 4,800,159, and 4,965,188, and "PCR Protocols: A guide to method and applications" edited by Innis et al.

In the step of determining the existence of a polymorphism or mutation in DNA, a detection method using homology between a mutant gene and a normal gene may be used. Examples of such method include the nucleotide sequence determination method (Applied Biosystems) and the TILLING method comprising detecting a mutant using an enzyme capable of cleaving one member of a mismatch pair (Till et al., 2003, Genome Res 13: 524-530). Detection can be carried out by comparing sequence data obtained by such method with the nucleotide sequence of a gene fragment shown in SEQ ID NO: 2, 4, or 5 or the nucleotide sequence of a gene fragment shown in SEQ ID NO: 19, 21, or 22.

In the step of determining a difference in the mRNA amount, the above cDNA is subjected to quantitative PCR which may be, for example, real-time PCR (with, for example, a LightCycler® (Roche Diagnostics)) with the use of primers produced based on the nucleotide sequence shown in SEQ ID NO: 2 or SEQ ID NO: 4 or the nucleotide sequence shown in SEQ ID NO: 19 or 21. Then, a difference in the mRNA amount can be determined based on a comparison of the obtained result and the cDNA amount derived from the variety, "Sassy".

In a particularly preferable embodiment, the above defined method for determining the existence of a mutation of a glycoalkaloid biosynthetic enzyme gene is applied to a material obtained from a potato (*Solanum tuberosum*), which is a solanaceous plant (Solanaceae).

According to the above mutation and/or polymorphism determination method, a mutation or polymorphism of a gene encoding a glycoalkaloid biosynthetic enzyme can be identified at the nucleotide level. In addition, a plant in which a gene encoding a glycoalkaloid biosynthetic enzyme has a mutation and/or polymorphism can be selected. The present invention encompasses the thus obtained plant in which a gene encoding a glycoalkaloid biosynthetic enzyme has a mutation and/or polymorphism.

In addition, by determining a mutation or polymorphism or differences in the mRNA amount and by analysing a glycoalkaloid content described below, a plant in which the ability to express a gene encoding a glycoalkaloid biosynthetic enzyme or the activity of a glycoalkaloid biosynthetic enzyme has been altered can be selected.

Here, "alteration of the ability to express a gene encoding a glycoalkaloid biosynthetic enzyme or the activity of a glycoalkaloid biosynthetic enzyme" refers to a modification of the ability to express a gene or glycoalkaloid biosynthetic enzyme activity caused by mutation such as artificial mutation, and an alteration in the ability to express a gene or glycoalkaloid biosynthetic enzyme activity due to the existence of a polymorphism.

"Modification of the glycoalkaloid biosynthetic enzyme activity in a plant caused by mutation" refers to modification of such activity in an existing variety of a plant species of interest. Such existing varieties include wild-type varieties. However, even if a wild-type variety is a naturally occurring variety, it is not included among the existing varieties if it is not an existing industrially applicable variety. The existing varieties include all varieties that have been confirmed to exist when a plant in which the glycoalkaloid biosynthetic enzyme activity has been modified has been obtained. A variety produced by artificial manipulation such as hybridization or gene manipulation is also included. In addition, in the case of modification of the activity, alteration in the activity does not necessarily take place compared to all existing varieties. If the activity in a specific existing variety is modified, the modified variety can be included among plants having modified glycoalkaloid biosynthetic enzyme activity. Such "plants having modified glycoalkaloid biosynthetic enzyme activity" also include plants in which activity has been modified via spontaneous mutation without artificial manipulation. By the method of the present invention, a plant in which activity has been altered spontaneously can be selected and established as a new variety. In addition, in a case in which an existing variety is subjected to mutagenesis treatment so as to produce a plant having modified glycoalkaloid biosynthetic enzyme activity, the plant compared with the produced plant may be an existing variety identical to the variety subjected to mutagenesis treatment. Alternatively, it may be a different existing variety. Further, it is also possible to obtain a novel plant variety in which the mutation in the gene is fixed and the ability to express a glycoalkaloid biosynthetic enzyme gene or glycoalkaloid biosynthetic enzyme activity has been modified. Such plants can be obtained by crossing plants selected from nature or produced by mutagenesis treatment, and having a mutation or polymorphism in the gene encoding a glycoalkaloid biosynthetic enzyme.

If a plant is a potato (*Solanum tuberosum*), examples of existing varieties thereof include "Cynthia," "Sassy," "Cheme," "Irish Cobbler (i.e., Danshaku)," "May Queen," and "Sayaka (Norin registration number: Norin No. 36)." Here, "a plant in which the ability to express a gene encoding a glycoalkaloid biosynthetic enzyme or glycoalkaloid biosynthetic enzyme activity has been modified compared with an existing variety" refers to a plant in which the ability to express a gene encoding a glycoalkaloid biosynthetic enzyme has been enhanced or reduced compared with an existing variety. It further refers to a plant in which glycoalkaloid biosynthetic enzyme activity has increased or decreased compared with an existing variety. The present invention also encompasses a plant in which the ability to express a gene encoding a glycoalkaloid biosynthetic enzyme or glycoalkaloid biosynthetic enzyme activity has been modified compared with an existing variety.

A plant in which the activity of biosynthetic enzyme of a glycoalkaloid that is a toxic substance has decreased is particularly preferable. In such plant, the amount of a glycoalkaloid biosynthetic enzyme synthesized is low or a glycoalkaloid biosynthetic enzyme cannot be synthesized. Also, the glycoalkaloid biosynthetic enzyme content is low or a glycoalkaloid biosynthetic enzyme is absent in the plant. Alternatively, the glycoalkaloid biosynthetic enzyme activity is low or nonexistent in the plant. Accordingly, the plant has low glycoalkaloid content or lacks glycoalkaloids. For instance, if the plant is a potato, a glycoalkaloid such as chaconine or solanine is not synthesized, and thus the amount of a synthesized or existing glycoalkaloid such as chaconine or solanine in the potato tubers is low. In addition, if the plant is a tomato, a glycoalkaloid such as tomatine is not synthesized, and thus the amount of a synthesized or existing glycoalkaloid such as tomatine in tomato fruits is low.

If the plant in which the glycoalkaloid biosynthetic enzyme activity is low or nonexistent is a potato, a glycoalkaloid such as chaconine or solanine is not synthesized in tubers, or the amount of a glycoalkaloid such as chaconine or solanine synthesized in tubers is lower than that in an existing variety described above. Also, in such a case, the content of a glycoalkaloid such as chaconine or solanine present in tubers may be low.

7. Glycoalkaloid Analysis and Purification

Known glycoalkaloid content analysis methods and glycoalkaloid purification methods using liquid chromatography have been disclosed by, for example, Matsuda et al. (Phytochem. Anal. 15:121-124, 2004) and Kozukue et al. (J. Agric. Food Chem. 52: 2079-2083, 2004). However, in any case, pretreatment of samples is labor-consuming, sufficient measurable limits cannot be achieved, or the use of a strong acid imposes a burden upon a column or apparatus. This has been problematic. Therefore, according to the present invention, the method using liquid chromatography with an alkali-resistant reversed-phase chromatography column capable of efficiently purifying GAs (glycoalkaloids) and performing high-precision analysis (disclosed in JP Patent Application No. 2009-170317) can be used. An example in which this method is applied to a potato (*Solanum tuberosum* L.) is described in Example 5.

Any column can be used as a column in the above method as long as it is an excellent alkali-resistant column. An example of an excellent alkali-resistant column that can be used is an ethylene-crosslinked column. Preferably, a column with the brand name of Xbridge™ (Waters) is used. Particularly preferably, the Waters XBridge™ Shield RP18 (Waters) and the Waters XBridge™ C18 are used. According to the method of the present invention, the XBridge™ Shield RP18 column is advantageous in that the time required for treatment of a single sample is short. Meanwhile, the Waters XBridge™ C18 column is advantageous in that it has good durability.

An alkaline buffer can be used as a mobile phase for liquid chromatography. Preferably, a volatile alkaline buffer is used. When a sample purified by liquid chromatography is subjected to mass spectrometry, it is convenient to use a volatile alkaline buffer as a mobile phase so as to prevent the alkaline buffer from remaining in the sample. Examples of a volatile alkaline buffer that can be used include triethylamine and ammonium hydrogen carbonate. However, ammonium hydrogen carbonate having excellent buffering effects is preferably used.

The concentration of ammonium hydrogen carbonate used as a mobile phase is 5 to 20 mM, preferably 5 to 15 mM, and more preferably 10 mM. The pH of ammonium hydrogen carbonate can be adjusted to preferably pH 9.0 to 11.0 and more preferably the pH 10.0. If the pH of a mobile phase is adjusted to 10.0, the buffering performance of ammonium hydrogen carbonate can be further improved.

GAs may be eluted into a mobile phase using an alkaline buffer and an organic solvent with an isocratic method or a gradient method. However, it is preferable to carry out elution with an isocratic method, which is convenient in terms of operation.

Examples of an organic solvent that can be used for a mobile phase include, but are not limited to, methanol, ethanol, tetrahydrofuran (THF), and acetonitrile (MeCN). Preferably, MeCN is used.

In an isocratic method, an alkaline buffer and an organic solvent, which are preferably an ammonium hydrogen carbonate solution and MeCN, are adequately used at a ratio of 30:70 to 70:30 and preferably 40:60 to 60:40 depending on the type of the GA of interest. For instance, if the GA of interest is α-solanine or α-chaconine, an alkaline buffer and an organic solvent, which are preferably an ammonium hydrogen carbonate solution and MeCN, are used at a ratio of 40:60. If the GA of interest is α-tomatine, an alkaline buffer and an organic solvent, which are preferably an ammonium hydrogen carbonate solution and MeCN, are used at a ratio of 60:40.

Liquid chromatography can be carried out using a commercially available HPLC apparatus. Column equilibration and flow rate can be adequately determined depending on the column size or sample volume.

Fractions obtained by liquid chromatography can be analyzed using mass spectrometry, a UV or multi-wavelength detector, or the like described below.

Preferably, a plant-derived sample is pretreated as described below prior to liquid chromatography for crude purification.

A plant-derived sample contains GAs and various polymers as foreign substances (e.g., starch, proteins, and cellulose). Thus, it is necessary to remove polymers contained as foreign substances in a sample and subject GAs to crude purification and washing in order to achieve efficient purification and high-precision analysis of GAs.

As a method for removing polymers as foreign substances, a general method used by a person skilled in the art such as an alcohol precipitation method can be used. Ethanol or methanol can be used as alcohol. However, methanol is preferable. In such case, acid is added to alcohol so as to extract GAs in salt form with good efficiency. Examples of acids that can be used include, but are not limited to, acetic acid, hydrochloric acid, and formic acid. Preferably, formic acid is added. The amount of acid added to alcohol is adequately determined so that the GA of interest is not damaged. If formic acid is used, it is added to alcohol so as to result in a concentration of 0.1% to 2% (v/v) and preferably 0.1% (v/v). If an acid other than formic acid is used, it can be added until the concentration thereof reaches the level equivalent to the above normality of added formic acid.

In the case of a conventional sample preparation method (see Matsuda et al., Phytochem. Anal. 15: 121-124, 2004), lengthy and complex pretreatment is required. This comprises steps of homogenizing a sample for many hours, carrying out centrifugation a plurality of times to remove polymers contained in the sample in large amounts as foreign substances such as starch, and filtering the resultant. Meanwhile, according to the preparation method of the present invention, it is possible to rapidly remove polymers as foreign substances such as starch via alcohol precipitation from plant pieces obtained by rapid disruption as described above. Therefore, sample preparation can be carried out in a short time in a convenient manner.

After alcohol precipitation, the supernatant containing GAs is diluted with acid such as 0.1% to 2% (v/v) formic acid or acetic acid and preferably 0.1% (v/v) formic acid. The dilution is subjected to liquid chromatography under the above conditions.

Fractions purified via liquid chromatography can be further subjected to mass spectrometry. In such case, mass spectrometry may be carried out by LC-MS, which is a technique that combines liquid chromatography with mass spectrometry.

Mass spectrometry can be carried out by sector field mass spectrometry, double-focusing sector field mass spectrometry, quadrupole mass spectrometry, quadrupole ion trap mass spectrometry, time-of-flight mass spectrometry, ion-cyclotron mass spectrometry (Fourier transform mass spectrometry), or the like.

Examples of a method for ionizing a sample for mass spectrometry that can be used include an EI (electron ionization) method, a CI (chemical ionization) method, a DEI (desorption electron ionization) method, a DCI (desorption chemical ionization) method, an FAB (fast atom bombardment) method, an FRIT-FAB (FRIT-fast atom bombardment) method, an ESI (electrospray ionization) method, and an MALDI (matrix-assisted laser desorption ionization) method.

Mass spectrometry conditions are specifically described in the Examples. However, a person skilled in the art can adequately determine conditions depending on the type of GA used as an analyte.

It is possible to analyze reference analytes of GAs using LC-MS to create a calibration curve according to a general method used by a person skilled in the art. β-D-glucosamine pentaacetate can be used as an internal reference substance for a potato-derived sample, particularly in an α-solanine or α-chaconine analysis system. However, it is preferable to use brassinolide having a steroid skeleton similar to that of α-solanine or α-chaconine. Meanwhile, a water-soluble amine is preferably used for a tomato-derived sample, particularly in an α-tomatine analysis system. Examples of a water-soluble amine that can be used as an internal reference substance include serinemethyl ester and alanine methyl ester. However, alanine methyl ester is particularly preferable because sufficient retention in a column is achieved. Therefore, the reliability of quantitative analysis can be significantly improved using brassinolide for a potato-derived sample and alanine methyl ester for a tomato-derived sample.

According to the method of the present invention, a column with a size widely used for HPLC can be used. The conditions used herein can be directly applied to analysis using a UV or multi-wavelength detector.

EXAMPLES

The present invention is hereafter described in greater detail with reference to the following examples, although the present invention is not limited thereto.

Example 1

Acquisition of the Full-Length Sequence of Candidate Glycoalkaloid Biosynthetic Gene C mRNA was extracted from sprouts of a potato (*Solanum tuberosum*) variety, "Sassy" using RNeasy (QIAGEN). Total cDNA synthesis was carried out using a SuperScript First-Strand System (Invitrogen). It is said that aglycone of a glycoalkaloid is formed with cholesterol, but this has not been proved (Non-Patent Literature 1). However, assuming that the aglycone is formed with a cholesterol-related compound, there must be some steps of hydroxylation. In this case, at least three types of enzymes (i.e., cytochrome P450 monooxygenase, dioxygenase, and/or NADPH-flavin reductase) are probably involved in the steps of hydroxylation. Of these, cytochrome P450 monooxygenase was designated herein as a target. As a gene expressed in a potato, the TC135549 gene, for which many EST clones have been isolated from sprouts, was selected based on the information disclosed in Release 11.0 of the DFCI Potato Gene Index (compbio.dfci.harvard.edu/tgi/plant.html).

PCR was performed based on the above sequence using primers (U841: GCTTGCTCTGTTCTTGTACATCTC (SEQ ID NO: 6); and U842: TGAAAAGCAGAATTAGCAGCA (SEQ ID NO: 7)) (PCR conditions: 95° C. for 5 minutes; 30 cycles of 95° C. for 30 seconds, 55° C. for 30 seconds, and 72° C. for 3 minutes; and 72° C. for 10 minutes). The amplification product was subjected to cloning using a TOPOTA cloning kit for sequencing (Invitrogen). Further, the nucleotide sequence was determined using an ABI310 (Applied Biosystems). The sequence comprising the ORF region is shown in SEQ ID NO: 2 and the amino acid sequence of an enzyme encoded by the cDNA sequence is shown in SEQ ID NO: 1. The homologous gene of tomato used herein corresponds to TC192845 in the DFCI Tomato Gene Index as in the above case. The sequence comprising the ORF region is shown in SEQ ID NO: 4 and the amino acid sequence of an enzyme encoded by the cDNA sequence is shown in SEQ ID NO: 3. As a result of a comparison of the nucleotide sequences of these genes, homology therebetween was found to be 95% (FIG. 1). In addition, the homologous gene of tomato was identical to the sequence reported by Bartoszewski et al. (Acta Physiol. Plant. 22, 269-271 (2000)). Bartoszewski et al. reported that a sequence homologous (75%) to the sequence of CYP72A2 found in tobacco was identified, that wound-induced expression of the gene takes place, that the gene exhibits circadian rhythm, and that the gene is frequently expressed in young tissues. However, no results or discussions about the functions of the gene were reported. Therefore, nothing about the involvement of the gene in glycoalkaloid biosynthesis was reported.

Example 2

Isolation of the Genomic Gene of Candidate Glycoalkaloid Biosynthetic Gene C

Genomic DNA was extracted from "Sassy" using RNeasy (QIAGEN). PCR was performed using the primers used in Example 1 for determination of the nucleotide sequence of the full-length genomic DNA (SEQ ID NO: 5). The DNA was found to contain four introns.

Example 3

Vector Construction for Production of a Transformant Having the Suppressed Candidate Glycoalkaloid Biosynthetic Gene C The above gene was suppressed through transformation by a method comprising inducing expression of a gene fragment of a reverse complementary strand structured to be driven by a powerful promoter (which is generally referred to as an RNAi method for plants) (Chuang and Meyerowitz, Proc Natl Acad Sci, USA, 97, 4985-90 (2000); Wesley et al., Plant J., 27, 581-90 (2001)). The full-length cDNA obtained in Example 1 was subjected to PCR using primers (U724: GAGCTCTAGAGAAGCAAAGAAAACACC (SEQ ID NO: 8); and U725: GGATCCATATGCTAACCAATTC-CTCCCATC (SEQ ID NO: 9)) (PCR conditions: 95° C. for 5 minutes; 30 cycles of 95° C. for 30 seconds, 55° C. for 30 seconds, and 72° C. for 30 seconds; and 72° C. for 10 minutes). Thus, a gene fragment was obtained. A pKT226 vector for plant transformation was prepared using a pKT11 binary vector (JP Patent Publication (Kokai) No. 2001-161373 A) as a reference vector by ligating a cauliflower mosaic virus 35S RNA promoter, the gene fragment (in the forward direction), the 7th intron of the *Arabidopsis thaliana* phytoene desaturase gene (AT4g14210), the gene fragment (in the reverse direction), and a cauliflower mosaic virus 35S RNA terminator in such order (FIG. 2).

Example 4

Production of a Transformed Potato Plant

The vector prepared in Example 3 was introduced into the *Agrobacterium tumefaciens* GV3110 strain by the electroporation method (Gelvin and Schilperoor, Plant Molecular Biology Manual, C2, 1-32 (1994), Kluwer Academic Publishers). The *Agrobacterium tumefaciens* GV3110 strain comprising the vector was subjected to shake culture in a YEB liquid medium supplemented with 50 ppm Kanamycin (5 g/l beef extract, 1 g/l yeast extract, 5 g/l peptone, 5 g/l sucrose, and 2 mM magnesium sulfate (pH7.2)) at 28° C. for 12 hours. The culture liquid (1.5 ml) was centrifuged at 10,000 rpm for 3 minutes for harvest, followed by washing with an LB medium (1 ml) for removal of Kanamycin. Further, centrifugation was performed at 10,000 rpm for 3 minutes for harvest. The resultant was resuspended in an MS medium containing 3% sucrose (1.5 ml) (Murashige & Skoog, Physiol. Plant., 15, 473-497 (1962)). Thus, a bacterial suspension for infection was obtained.

Transformation of a potato was carried out according to a conventional method (Monma (1990), Plant Biotechnology 7: 57-63). Microtubers obtained from a potato variety, "Sassy" (Kirin Agribio Company, Limited.) were sliced to thicknesses of 2 to 3 mm, and thus materials for *Agrobacterium* infection were prepared. The slices were immersed in the above *Agrobacterium* cell suspension and then placed on sterilized filter paper for removal of excessive *Agrobacterium* cells. The slices were placed on an MS medium (supplemented with Zeatin (1 ppm), IAA (0.1 ppm), acetosyringone (100 µM), and agar (0.8%)) in a petri dish. Culture was carried out under conditions comprising illumination for 16 hours (photon flux density: 32 µE/m$^2$s)/non-illumination for 8 hours at 25° C. for 3 days. Next, culture was carried out in a medium supplemented with carbenicillin (250 ppm) instead of acetosyringone for 1 week. Then, the culture product was further transferred onto a medium supplemented with Kanamycin (50 ppm), followed by subculture at 2-week intervals. During subculture, adventitious bud formation and then shoot formation took place. The grown shoots were placed on an MS medium containing carbenicillin (250 ppm) and Kanamycin (100 ppm) and lacking plant growth regulators. Each individual having a Kanamycin-resistant gene as a foreign gene was detected from among Kanamycin-resistant plants grown from the rooting shoots by PCR (PCR conditions: 95° C. for 5 minutes; 30 cycles of 95° C. for 30 seconds, 55° C. for 30 seconds, and 72° C. for 1 minute; and 72° C. for 10 minutes), thereby confirming that the redifferentiated plant was a transformed plant. Here, the following primers were used as primers capable of specifically amplifying the Kanamycin-resistant gene sequence: TAAAGCACGAGGAAGCGGT (SEQ ID NO: 10); and GCACAACAGACAATCGGCT (SEQ ID NO: 11). Accordingly, 28 transformed potato plant lines transfected with the pKT226 vector were obtained.

Example 5

Analysis of the Glycoalkaloid Content and the Expression of Candidate Gene C in Transformed Plants In vitro stems of the 28 lines obtained in Example 4 were allowed to grow for one month after subculture. Two to four stems were collected to adjust the weight to approximately 100 mg. The glycoalkaloid content was determined by the method comprising liquid chromatography using an alkali-resistant reversed-phase chromatography column (which has been disclosed in Japanese Patent Application No. 2009-170317) described below.

Analysis of GAs (α-Solanine and α-Chaconine) Contained in a Potato

1. Sample Preparation

In vitro stems of the 28 individuals obtained in Example 4 were allowed to grow for one month after subculture. Two to four stems were collected to adjust the weight to approximately 100 mg. 80% MeOH aq. (990 µl) containing 0.1% formic acid and brassinolide (Brassino Co., Ltd.) (10 µg/10 µL) used as an internal reference were added thereto, followed by disruption using a mixer mill (½s sec, 5 min, 4° C.). The obtained disruptant was centrifuged (10,000 rpm, 5 min), followed by alcohol precipitation. Then, a portion of the supernatant (25 µl) was collected and adjusted to 500 µL with a 0.1% formic acid solution. The thus obtained sample was subjected to LC-MS under the conditions described below. LCMS-2010EV (Shimadzu Corporation) was used as an LC-MS apparatus.

2. LC-MS Conditions (i) LC Conditions

An ethylene-crosslinked column (XBridge™ Shield RP18-5 (4) 2.1×150 mm, Waters)) having excellent alkali resistance was employed for the LC system. The following mobile phases were used at a ratio of A:B=40:60 with the above sample solvent under isocratic conditions: mobile phase A: 10 mM ammonium hydrogen carbonate solution (pH 10); and mobile phase B: MeCN. Other conditions applied herein are described below.

Flow rate: 0.2 mL/min
Column oven: 40° C.
(ii) MS Conditions

First, the MS spectrum for each component was confirmed via scan mode (see FIG. 3). As a result, a detection method was used via SIM mode (m/z: 481 (brassinolide), 869 (α-solanine), and 853 (α-chaconine)).

Other MS conditions used herein are described below.
MS detection: Positive ion mode
Ionization method: ESI
Event time: 1 sec
Detector voltage: 1.5 kV
Analysis time: 8 min 3. Creation of Calibration Curves Using Reference Products (α-Solanine, α-Chaconine, and Brassinolide)

α-solanine (Wako Pure Chemical Industries, Ltd.) (2 mg) and α-chaconine (Sigma-Aldrich) (2 mg) were separately dissolved in a 0.1% (v/v) formic acid solution (1 mL) (so as to obtain a 2 μg/μL solution for each product). Equivalent volumes of the two different solutions were mixed so as to prepare a solution containing α-solanine and α-chaconine at a concentration of 1 μg/μL (=1000 ng/μL). The solution was diluted 10 times with a 0.1% (v/v) formic acid solution in a stepwise manner, followed by LC-MS. Thus, calibration curves were created. In addition, measurable limits of the both substances were obtained.

Brassinolide (Brassino Co., Ltd.) (1 mg) was dissolved in an MeOH solution (1 mL) (1 μg). The resulting solution was diluted 10 times with 50% (v/v) aqueous MeOH in a stepwise manner, followed by LC-MS. Thus, a calibration curve was created.

FIG. 4 shows calibration curves created for α-solanine, α-chaconine, and brassinolide. Good linearity with a confidence coefficient of 0.99 or more was confirmed within the range of 0.05 to 50 ng for α-solanine and α-chaconine as shown in FIG. 4. For the both substances, when the content exceeded 100 ng, signal saturation was observed, resulting in loss of linearity. In addition, the measurable limit was 0.02 ng (2 μL per injection) for both substances.

Meanwhile, good linearity was confirmed within the range of 2 to 200 ng for brassinolide (see FIG. 4). When the content was not less than 500 ng, this caused signal saturation as in the above case.

Figure 5:
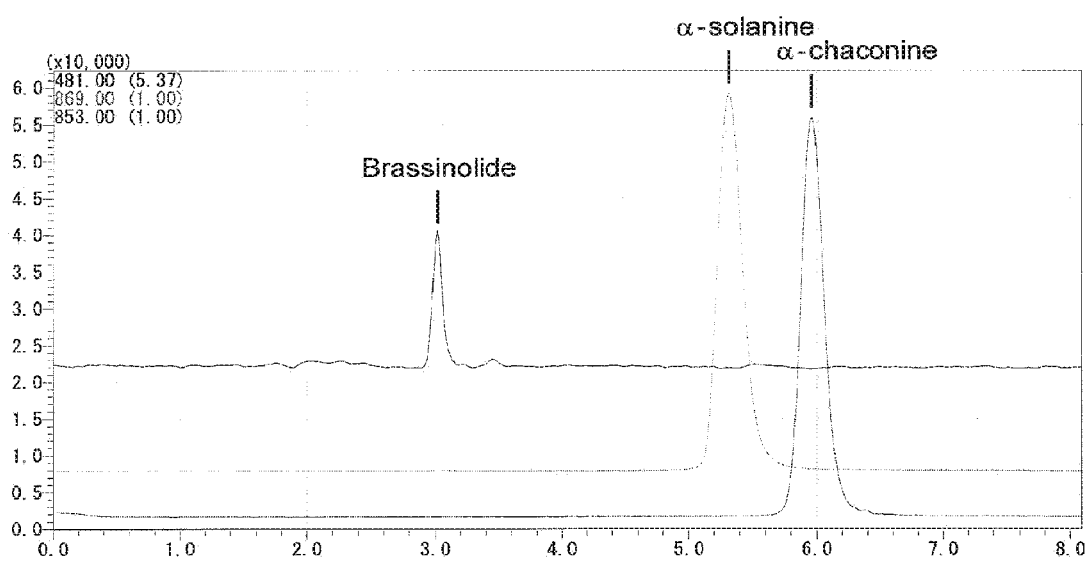
FIG. 5 shows LC-MS chromatograms for reference products (α-solanine, α-chaconine, and brassinolide).

FIG. 5 shows typical chromatograms of the reference products (α-solanine, α-chaconine, and brassinolide).

4. LC-MS Analysis of GAs in a Potato Using Brassinolide as an Internal Reference Each sample prepared in 1 above (10 μl, or 20 μL) was injected into an LC-MS system under the above conditions.

The recovery rate of brassinolide used as an internal reference was found to be 50% to 110%. Correction was carried out based on the quantitative value of brassinolide, followed by quantitative determination of the amounts of α-solanine and α-chaconine in each sample based on the above calibration curves. The amounts of α-solanine and α-chaconine per 100 mg (FW) of each sample were calculated.

Figure 6:
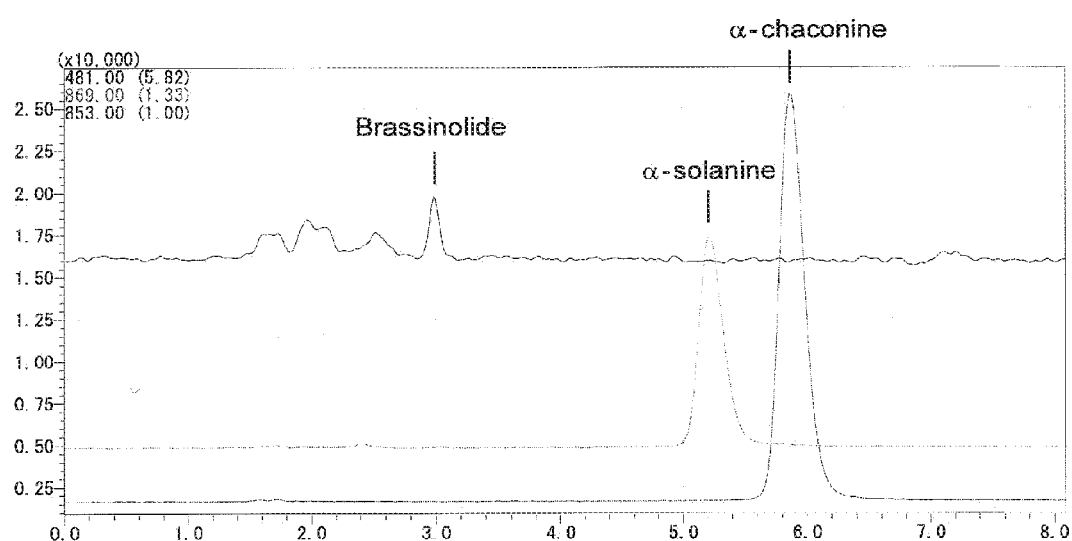
FIG. 6 shows LC-MS chromatograms for α-solanine, α-chaconine, and brassinolide in a stem-derived sample.

FIG. 6 shows typical chromatograms for the analysis.

Figure 7:
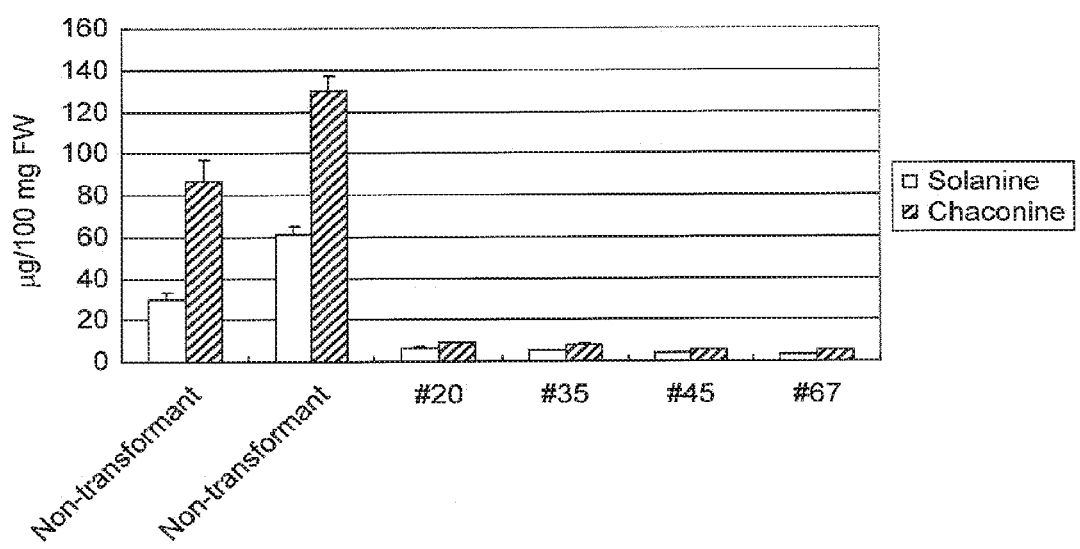
FIG. 7 is a chart showing the glycoalkaloid contents in in vitro stems of potato transformants. Each error bar indicates a standard deviation.
Figure 8:
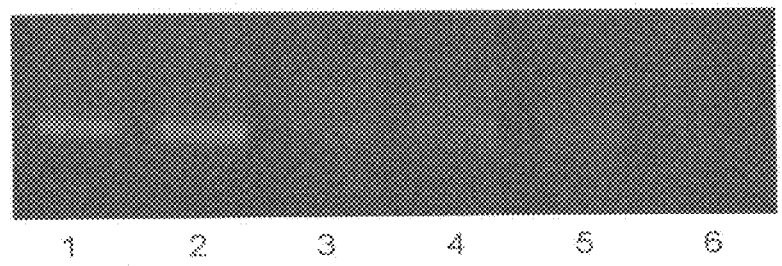
FIG. 8 shows RT-PCR results for mRNAs extracted from in vitro stems of potato transformants.

The amounts of accumulated glycoalkaloids were found to be low with good reproducibility in 4 lines (#20, #35, #45, and #67) selected from among 28 lines. Therefore, as described above, in vitro stems of the 4 lines were disrupted in liquid nitrogen. A half portion of each disruptant was used for determination of the glycoalkaloid content. The other half portion thereof was subjected to mRNA extraction using RNeasy (QIAGEN). Total cDNA synthesis was carried out using a SuperScript First-Strand System (Invitrogen). The amounts of accumulated glycoalkaloids in individual of these lines were found to be remarkably lower than those in a non-transformant (2 individuals) (FIG. 7). Further, as a result of RT-PCR using primers (U724: GAGCTCTAGAGAAGCAAAGAAAACACC (SEQ ID NO: 12); and U840: GGGCATGAACATAGGAAGGA (SEQ ID NO: 13)), it was found that mRNA was expressed at a remarkably low level or was impossible to observe in any of the individuals (FIG. 8). These results revealed that suppression of expression of the candidate gene C caused significant reduction of glycoalkaloid accumulation, and they also revealed that the candidate gene C was a gene encoding a glycoalkaloid biosynthetic enzyme. The in vitro plants of the 4 lines were allowed to proliferate with the non-transformant. Three individuals of each line were habituated in commercially available culture soil for vegetables and cultivated in a biohazard greenhouse according to a general method, followed by harvest of tubers. Each of the individuals of the 4 lines (#20, #35, #45, and #67) was found to be comparable in growth to the non-transformant. Although line #35 was found to have a low average weight of 1 tuber, it was possible to harvest tubers having average weights comparable to the average weight of the non-transformant (table 1).

TABLE 1

| Potato transformant tuber yield | | | | | |
|---|---|---|---|---|---|
| Line number | Number of tubers | Standard deviation | Average weight of 1 tuber (g) | Total weight of 1 stock (g) | Standard deviation |
| Non-transformant | 9.7 | 5.5 | 13.4 | 129.3 | 60.8 |
| #20 | 8.7 | 3.8 | 15.2 | 131.7 | 6.4 |
| #35 | 12.0 | 5.0 | 8.5 | 102.2 | 40.9 |
| #45 | 12.3 | 3.5 | 12.1 | 149.2 | 4.9 |
| #67 | 11.3 | 1.2 | 11.1 | 125.5 | 5.2 |

Figure 9:
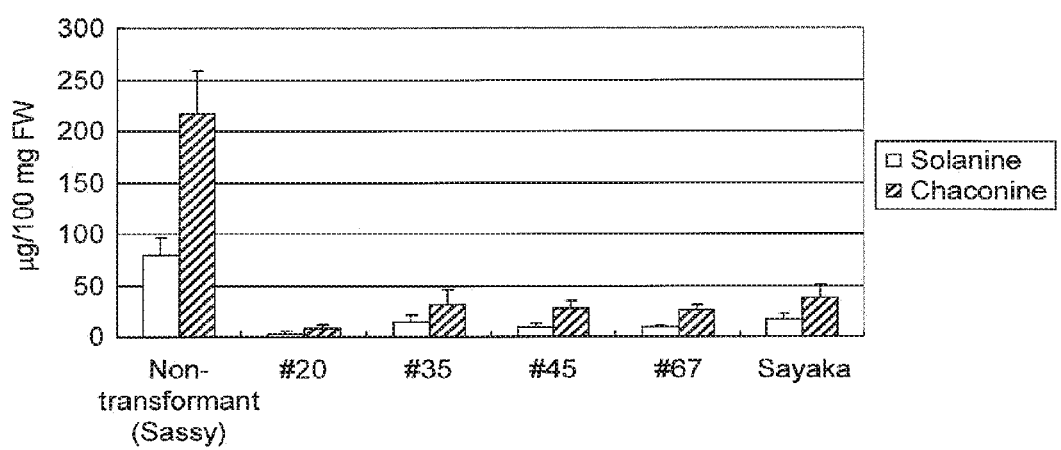
FIG. 9 is a chart showing the glycoalkaloid contents in tuber epidermis of potato transformants. Each error bar indicates a standard deviation.
Figure 10:
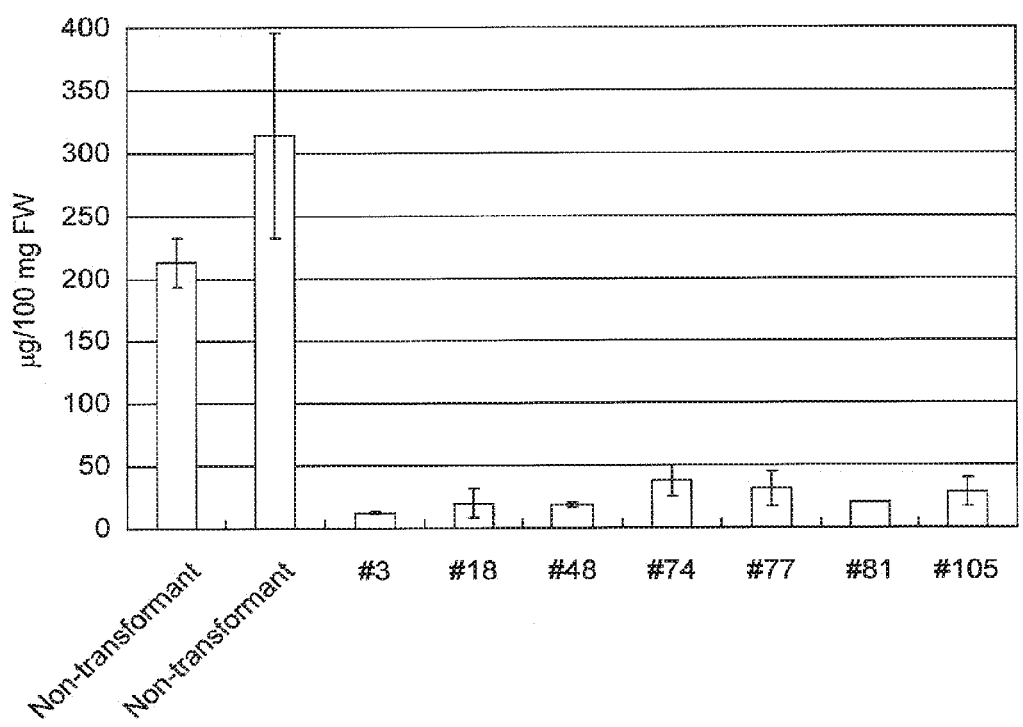
FIG. 10 is a chart showing the glycoalkaloid contents in leaves of tomato transformants. Each error bar indicates a standard deviation.

Further, the epidermis of the center portion of each of three harvested tubers of each line was peeled to result in thicknesses of approximately 1 mm. Then, the glycoalkaloid content was analyzed in the above manner. As a result, surprisingly, it was confirmed that the glycoalkaloid content in tubers was extremely low, having a value that was lower than that determined in the same manner for "Sayaka," which is a variety known to have low glycoalkaloid content (FIG. 9)

Example 6

Production of Transformed Tomato Plants

Tomato transformation was carried out according to a conventional method (Sun et al. (2006) Plant Cell Physiol. 47: 426-431). The *Agrobacterium tumefaciens* AGLO strain comprising a pKT226 vector prepared in Example 3 was cultured so as to obtain a bacterial suspension for infection. Sections (thickness: 5 mm or less) of cotyledons of a plant of a tomato (*Solanum lycopersicum*) experimental line called "Micro-Tom" obtained via sterile seeding were immersed in the above *Agrobacterium* suspension for infection for 10 minutes and then placed on sterilized filter paper for removal of excessive *Agrobacterium* cells. The leaf sections were placed on a coculture MS medium (supplemented with zeatin (1.5 mg/l), acetosyringone (40 μM), and Gelrite® (0.3%)) (Murashige & Skoog, Physiol. Plant., 15, 473-497 (1962)) in a petri dish. The petri dish was subjected to culture in a dark place at 25° C. for 3 days. The sections were subjected to subculture at 2-week intervals using selective MS medium 1 (supplemented with zeatin (1.5 mg/l), Kanamycin (100 mg/l), Augmentin (375 mg/l), and Gelrite® (0.3%)) under conditions comprising illumination for 16 hours (photon flux density: 32 µE/m²s)/non-illumination for 8 hours at 25° C. During subculture, adventitious bud formation and then shoot formation took place. In order to allow the shoots to further grow, the shoots were transplanted to selective MS medium 2 (supplemented with zeatin (1.0 mg/l), Kanamycin (100 mg/l), Augmentin (375 mg/l), and Gelrite® (0.3%)). The grown shoots were rooted in a selective ½ concentration MS medium (supplemented with Kanamycin (100 mg/l), Augmentin (375 mg/l), and Gelrite® (0.3%)). Each individual having a Kanamycin-resistant gene as a foreign gene was detected from among Kanamycin-resistant plants grown from the rooting shoots by PCR (PCR conditions: 95° C. for 5 minutes; 30 cycles of 95° C. for 30 seconds, 55° C. for 30 seconds, and 72° C. for 1 minute; and 72° C. for 10 minutes), thereby confirming that the redifferentiated plant was a transformed plant. Here, the following primers were used as primers capable of specifically amplifying the Kanamycin-resistant gene sequence: TAAAGCACGAGGAAGCGGT (SEQ ID NO: 14); and GCACAACAGACAATCGGCT (SEQ ID NO: 15). Accordingly, 32 transformed tomato plant lines transfected with the pKT226 vector were obtained. The obtained 28 individuals were habituated in a greenhouse and cultivated for approximately 2 months. Three newly developed leaves were weighed to approximately 100 mg for each line. The glycoalkaloid content was determined as in the case of potato by the method comprising liquid chromatography using an alkali-resistant reversed-phase chromatography column described in Example 5. Note that, regarding analysis conditions, the following mobile phases were used at a ratio of A:B=60:40 with the above sample solvent under isocratic conditions: mobile phase A: 10 mM ammonium hydrogen carbonate solution (pH 10); and mobile phase B: MeCN. As a result, 7 out of 32 lines were found to have remarkably low tomatine content of 50 µg or less per 100 mg of fresh weight (FW) (FIG. 11).

Example 7

Screening of Plants with Mutation of Candidate Glycoalkaloid Biosynthetic Gene C Leaves were collected from 10 individuals of an in vitro plant obtained by subjecting a potato variety ("Sassy") to mutation treatment involving particle beam irradiation (an NIRS-HIMAC irradiation apparatus; a 0.1 Gy to 3 Gy argon ion beam (500 MeV/nucleon), a 0.2 Gy to 3 Gy neon ion beam (400 Mev/nucleon), or a 0.5 Gy to 5Gy carbon ion beam (290 MeV/nucleon)) (provided by Dr. Okamura (chief researcher), Kirin Agribio Company, Limited.). Then, genomic DNA was obtained using DNeasy. The structural gene of the genomic DNA was subjected to PCR (PCR conditions: 95° C. for 5 minutes; 30 cycles of 95° C. for 30 seconds, 55° C. for 30 seconds, and 72° C. for 5 minutes; and 72° C. for 10 minutes) using primers (U841: GCTTGCTCTGTTCTTGTACATCTC (SEQ ID NO: 16); and U842: TGAAAAGCAGAATTAGCAGCA (SEQ ID NO: 17)). Thus, the gene region was obtained. In addition, cloning was carried out using a TOPOTA cloning kit for sequencing. Further, the nucleotide sequence was determined using ABI310. As a result, it was found that a line having a mutated gene was not included among 10 stocks provided herein. However, it is possible to obtain a plant having a mutated gene by repeatedly carrying out the above procedures using a plant subjected to sufficient mutation treatment.

Example 8

Acquisition of the Full-Length Sequence of Candidate Glycoalkaloid Biosynthetic Gene D mRNA was extracted from sprouts of a potato (*Solanum tuberosum*) variety, "Sassy" using RNeasy (QIAGEN). Total cDNA synthesis was carried out using a SuperScript First-Strand System (Invitrogen). It is said that aglycone of a glycoalkaloid is formed with cholesterol, but this has not been proved (Non-Patent Literature 1). However, assuming that the aglycone is formed with a cholesterol-related compound, there must be some steps of hydroxylation. In this case, at least three types of enzymes (i.e., cytochrome P450 monooxygenase, dioxygenase, and NADPH-flavin reductase) are probably involved in the steps of hydroxylation. Of these, cytochrome P450 monooxygenase was designated herein as a target. As a gene expressed in a potato, the TC141445 gene, for which many EST clones have been isolated from sprouts, was selected based on the information disclosed in Release 11.0 of the DFCI Potato Gene Index (compbio.dfci.harvard.edu/tgi/plant.html).

PCR was performed based on the above sequence using primers (U883: AGCAATCAAACATGGGTATTG (SEQ ID NO: 23); and U876: TGATGTGAACTTGAGATTGGTG (SEQ ID NO: 24)) (PCR conditions: 95° C. for 5 minutes; 30 cycles of 95° C. for 30 seconds, 55° C. for 30 seconds, and 72° C. for 3 minutes; and 72° C. for 10 minutes). The amplification product was subjected to cloning using a TOPOTA cloning kit for sequencing (Invitrogen). Further, the nucleotide sequence was determined using an ABI310 (Applied Biosystems). The sequence comprising the ORF region is shown in SEQ ID NO: 19 and the amino acid sequence of an enzyme encoded by the cDNA sequence is shown in SEQ ID NO: 18. The homologous gene of tomato used herein corresponds to SGN-U567668 in the *Lycopersicon* Combined (Tomato) Unigenes in the sol genomics network (solgenomics.net/). The sequence comprising the ORF region is shown in SEQ ID NO: 21 and the amino acid sequence of an enzyme encoded by the cDNA sequence is shown in SEQ ID NO: 20. As a result of a comparison of the nucleotide sequences of these genes, homology therebetween was found to be 95% (FIG. 11). The genomic sequence of the homologous gene of tomato was identical to the sequence reported as SL1.00sc04687 with the genomic structure in the family Solanaceae genomic network (olgenomics.net/index.pl) which has been reported to comprise 4 introns. However, nothing about its functions has been reported on the website.

Example 9

Isolation of the Genomic Gene of Candidate Glycoalkaloid Biosynthetic Gene D

Genomic DNA was extracted from "Sassy" using RNeasy (QIAGEN). PCR was performed using the primers used in Example 1 for determination of the nucleotide sequence of the full-length genomic DNA (SEQ ID NO: 22). The DNA was found to contain four introns.

Example 10

Figure 12:
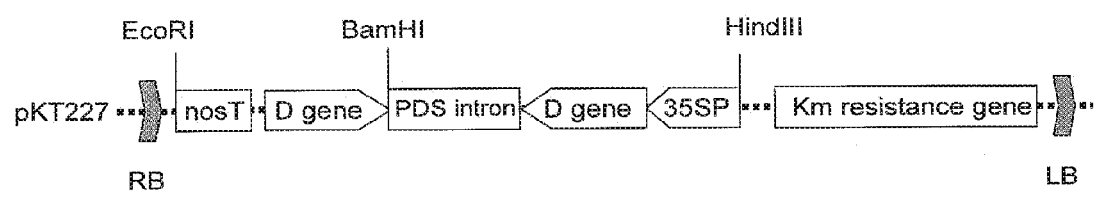
FIG. 12 shows a vector construct used for suppression of a candidate D gene.

Vector Construction for Production of a Transformant Having the Suppressed Candidate Glycoalkaloid Biosynthetic Gene D The above gene was suppressed through transformation by a method comprising inducing expression of a gene fragment of a reverse complementary strand structured to be driven by a powerful promoter (which is generally referred to as an RNAi method for plants) (Chuang and Meyerowitz, Proc Natl Acad Sci, USA, 97, 4985-90 (2000); Wesley et al., Plant J., 27, 581-90 (2001)). The full-length cDNA obtained in Example 1 was subjected to PCR using primers (U726: GAGCTCTAGAGGTTAAGAGTTTGTGCCAACG (SEQ ID NO: 25); and U727: GGATCCATATGGCTTTCTCTT-GCCAATCTG (SEQ ID NO: 26)) (PCR conditions: 95° C. for 5 minutes; 30 cycles of 95° C. for 30 seconds, 55° C. for 30 seconds, and 72° C. for 30 seconds; and 72° C. for 10 minutes). Thus, a gene fragment was obtained. A pKT227 vector for plant transformation was prepared using a pKT11 binary vector (JP Patent Publication (Kokai) No. 2001-161373 A) as a reference vector by ligating a cauliflower mosaic virus 35S RNA promoter, the gene fragment (in the forward direction), the 3rd intron of the *Arabidopsis thaliana* phytoene desaturase gene (AT4g14210), the gene fragment (in the reverse direction), and a nopaline synthetase gene terminator in such order (FIG. 12).

Example 11

Production of a Transformed Potato Plant

The vector prepared in Example 10 was introduced into the *Agrobacterium tumefaciens* GV3110 strain by the electroporation method (Gelvin and Schilperoor, Plant Molecular Biology Manual, C2, 1-32 (1994), Kluwer Academic Publishers). The *Agrobacterium tumefaciens* GV3110 strain comprising the vector was subjected to shake culture in a YEB liquid medium supplemented with 50 ppm Kanamycin (5 g/l beef extract, 1 g/l yeast extract, 5 g/l peptone, 5 g/l sucrose, and 2 mM magnesium sulfate (pH7.2)) at 28° C. for 12 hours. The culture liquid (1.5 ml) was centrifuged at 10,000 rpm for 3 minutes for harvest, followed by washing with an LB medium (1 ml) for removal of Kanamycin. Further, centrifugation was performed at 10,000 rpm for 3 minutes for harvest. The resultant was resuspended in an MS medium containing 3% sucrose (1.5 ml) (Murashige & Skoog, Physiol. Plant., 15, 473-497 (1962)). Thus, a bacterial suspension for infection was obtained.

Transformation of a potato was carried out according to a conventional method (Monma (1990), Plant Biotechnology 7: 57-63). Microtubers obtained from a potato variety, "Sassy" (Kirin Agribio Company, Limited.) were sliced to thicknesses of 2 to 3 mm, and thus materials for *Agrobacterium* infection were prepared. The slices were immersed in the above *Agrobacterium* cell suspension and then placed on stelirized filter paper for removal of excessive *Agrobacterium* cells. The slices were placed on an MS medium (supplemented with Zeatin (1 ppm), IAA (0.1 ppm), acetosyringone (100 μM), and agar (0.8%)) in a petri dish. Culture was carried out under conditions comprising illumination for 16 hours (photon flux density: 32 μE/m$^2$s)/non-illumination for 8 hours at 25° C. for 3 days. Next, culture was carried out in a medium supplemented with carbenicillin (250 ppm) instead of acetosyringone for 1 week. Then, the culture product was further transferred onto a medium supplemented with Kanamycin (50 ppm), followed by subculture at 2-week intervals. During subculture, adventitious bud formation and then shoot formation took place. The grown shoots were placed on an MS medium containing carbenicillin (250 ppm) and Kanamycin (100 ppm) and lacking plant growth regulators. Each individual having a Kanamycin-resistant gene as a foreign gene was detected from among Kanamycin-resistant plants grown from the rooting shoots by PCR (PCR conditions: 95° C. for 5 minutes; 30 cycles of 95° C. for 30 seconds, 55° C. for 30 seconds, and 72° C. for 1 minute; and 72° C. for 10 minutes), thereby confirming that the redifferentiated plant was a transformed plant. Here, the following primers were used as primers capable of specifically amplifying the Kanamycin-resistant gene sequence: TAAAGCACGAGGAAGCGGT (SEQ ID NO: 10); and GCACAACAGACAATCGGCT (SEQ ID NO: 11). Accordingly, 31 transformed potato plant lines transfected with the pKT227 vector were obtained.

Example 12

Analysis of the Glycoalkaloid Content and the Expression of Candidate Gene D in Transformed Plants Thirty one lines obtained in Example 11 were subjected to glycoalkaloid content measurement in the manner used in Example 5.

Figure 13:
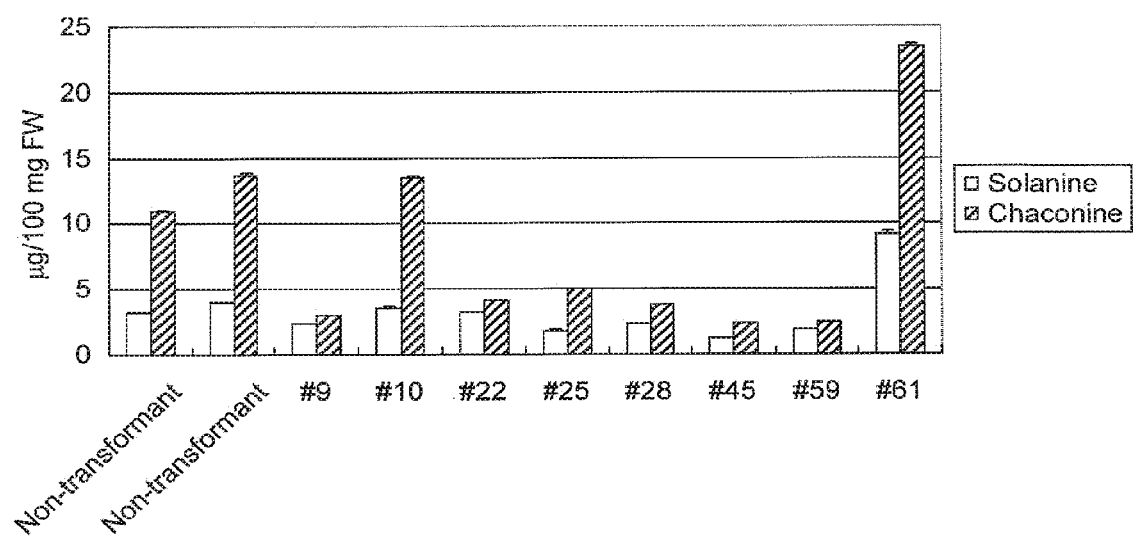
FIG. 13 is a chart showing the glycoalkaloid contents in in vitro stems of potato transformants. Each error bar indicates a standard deviation.
Figure 14:
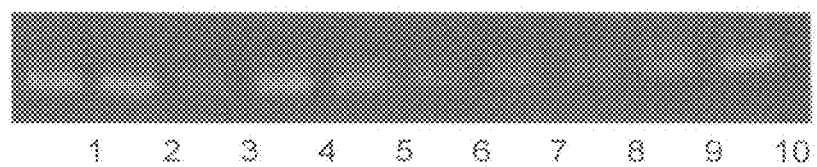
FIG. 14 shows RT-PCR results for mRNAs extracted from in vitro stems of potato transformants.

The amounts of accumulated glycoalkaloids were found to be low with good reproducibility in 4 lines (#9, #28, #45, and #59) selected from among 31 lines. Therefore, as described above, in vitro stems of the 4 lines were disrupted in liquid nitrogen. A half portion of each disruptant was used for determination of the glycoalkaloid content. The other half portion thereof was subjected to mRNA extraction using RNeasy (QIAGEN). Total cDNA synthesis was carried out using a SuperScript First-Strand System (Invitrogen). The amounts of accumulated glycoalkaloids in individuals of these lines were found to be remarkably lower than those in a non-transformant (2 individuals) (FIG. 13). Further, as a result of RT-PCR using primers (U871: TCGGGTGAGT-TCAGAAAACC (SEQ ID NO: 27); and U727: GGATC-CATATGGCTTTCTCTTGCCAATCTG (SEQ ID NO: 28)), it was found that mRNA was expressed at a remarkably low level or was impossible to observe in any of the individuals (FIG. 14). These results revealed that suppression of expression of the candidate gene D caused significant reduction of glycoalkaloid accumulation, and they also revealed that the candidate gene D was a gene encoding a glycoalkaloid biosynthetic enzyme. The in vitro plants of the 4 lines were allowed to proliferate with the non-transformant. Three individuals of each line were habituated in commercially available culture soil for vegetables (in a single planter) and cultivated in a biohazard greenhouse according to a general method, followed by harvest of tubers. Each of the individuals of the 4 lines (#9, #28, #45, and #59) was found to be comparable in growth to each non-transformant (of the two transformants in two planters). There were no differences in terms of the number of tubers among the transformants. Meanwhile, almost all of the transformants were found to be inferior to the non-transformants in terms of the average weight of a single tuber and the total weight of a single stock. However, it was possible to harvest tubers comparable to those of the non-transformants in terms of the conditions other than the weight (table 2).

TABLE 2

Potato transformant tuber yield

| Line number | Average number of tubers | Average weight of 1 tuber (g) | Total weight of 1 stock |
|---|---|---|---|
| Non-transformant | 9.3 | 20.6 | 192.2 |
| Non-transformant | 25.0 | 6.9 | 172.1 |
| #9 | 8.3 | 5.9 | 49.0 |
| #28 | 14.3 | 3.9 | 56.4 |
| #45 | 11.7 | 7.9 | 91.9 |
| #59 | 9.7 | 11.6 | 111.8 |

Figure 15:
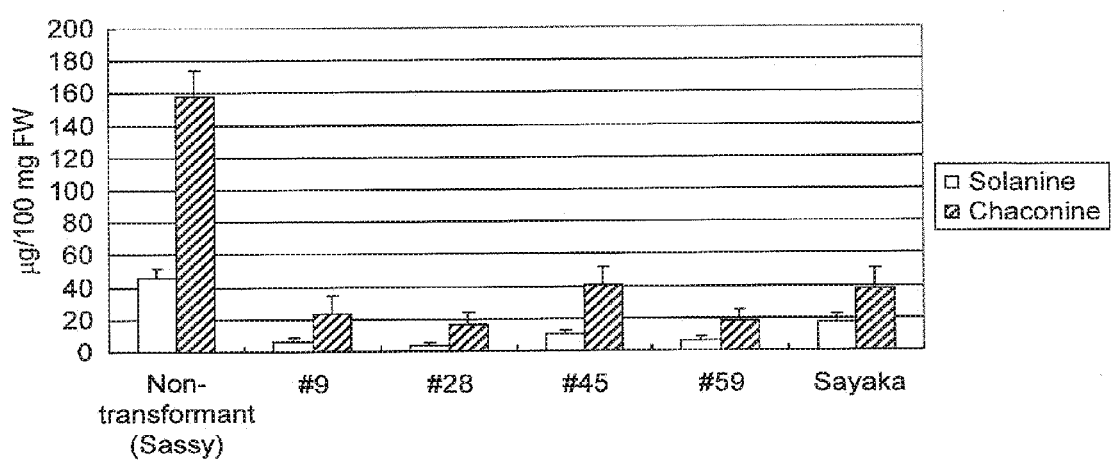
FIG. 15 is a chart showing the glycoalkaloid contents in tuber epidermis of potato transformants. Each error bar indicates a standard deviation.

Further, the epidermis of the center portion of each of three harvested tubers of each line was peeled to result in thicknesses of approximately 1 mm. Then, the glycoalkaloid content was analyzed in the above manner. As a result, surprisingly, it was confirmed that the glycoalkaloid content in tubers was extremely low, having a value that was lower than that determined in the same manner for "Sayaka," which is a variety known to have low glycoalkaloid content (FIG. 15)

Example 13

Production of Transformed Tomato Plants

Figure 16:
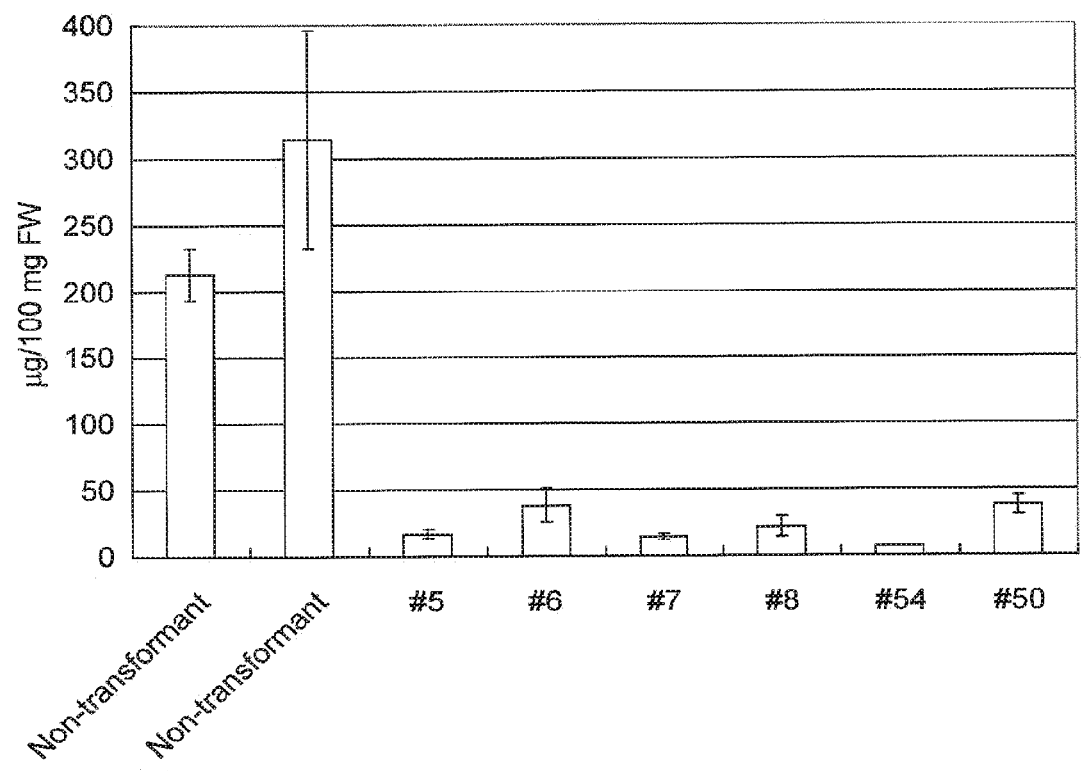
FIG. 16 is a chart showing the glycoalkaloid contents in leaves of tomato transformants. Each error bar indicates a standard deviation.

Tomato transformation was carried out according to a conventional method (Sun et al. (2006) Plant Cell Physiol. 47: 426-431). The *Agrobacterium tumefaciens* AGLO strain comprising a pKT227 vector prepared in Example 10 was cultured so as to obtain a bacterial suspension for infection. Sections (thickness: 5 mm or less) of cotyledons of a plant of a tomato (*Solanum lycopersicum*) experimental line called "Micro-Tom" obtained via sterile seeding were immersed in the above *Agrobacterium* suspension for infection for 10 minutes and then placed on sterilized filter paper for removal of excessive *Agrobacterium* cells. The leaf sections were placed on a coculture MS medium (supplemented with zeatin (1.5 mg/l), acetosyringone (40 µM), and Gelrite® (0.3%)) (Murashige & Skoog, Physiol. Plant., 15, 473-497 (1962)) in a petri dish. The petri dish was subjected to culture in a dark place at 25° C. for 3 days. The sections were subjected to subculture at 2-week intervals using selective MS medium 1 (supplemented with zeatin (1.5 mg/l), Kanamycin (100 mg/l), Augmentin (375 mg/l), and Gelrite® (0.3%)) under conditions comprising illumination for 16 hours (photon flux density: 32 µE/m$^2$s)/non-illumination for 8 hours at 25° C. During subculture, adventitious bud formation and then shoot formation took place. In order to allow the shoots to further grow, the shoots were transplanted to selective MS medium 2 (supplemented with zeatin (1.0 mg/l), Kanamycin (100 mg/l), Augmentin (375 mg/l), and Gelrite® (0.3%)). The grown shoots were rooted in a selective ½ concentration MS medium (supplemented with Kanamycin (100 mg/l), Augmentin (375 mg/l), and Gelrite® (0.3%)). Each individual having a Kanamycin-resistant gene as a foreign gene was detected from among Kanamycin-resistant plants grown from the rooting shoots by PCR (PCR conditions: 95° C. for 5 minutes; 30 cycles of 95° C. for 30 seconds, 55° C. for 30 seconds, and 72° C. for 1 minute; and 72° C. for 10 minutes), thereby confirming that the redifferentiated plant was a transformed plant. Here, the following primers were used as primers capable of specifically amplifying the Kanamycin-resistant gene sequence: TAAAGCACGAGGAAGCGGT (SEQ ID NO: 14); and GCACAACAGACAATCGGCT (SEQ ID NO: 15). Accordingly, 21 transformed tomato plant lines transfected with the pKT227 vector were obtained. The obtained 21 lines were habituated in a greenhouse and cultivated for approximately 2 months. Three newly developed leaves were weighed to approximately 100 mg for each line. The glycoalkaloid content was determined as in the case of potato by the method comprising liquid chromatography using an alkali-resistant reversed-phase chromatography column described in Example 5. Note that, regarding analysis conditions, the following mobile phases were used at a ratio of A:B=60:40 with the above sample solvent under isocratic conditions: mobile phase A: 10 mM ammonium hydrogen carbonate solution (pH 10); and mobile phase B: MeCN. As a result, 6 out of 21 lines were found to have remarkably low tomatine content of 50 µg or less per 100 mg of fresh weight (FIG. 16).

Example 14

Screening of Plants with Mutation of Candidate Glycoalkaloid Biosynthetic Gene D Leaves were collected from 10 individuals of an in vitro plant obtained by subjecting a potato variety ("Sassy") to mutation treatment involving particle beam irradiation (an NIRS-HIMAC irradiation apparatus; a 0.1 Gy to 3 Gy argon ion beam (500 MeV/nucleon), a 0.2 Gy to 3 Gy neon ion beam (400 Mev/nucleon), or a 0.5 Gy to 5Gy carbon ion beam (290 MeV/nucleon)) (provided by Dr. Okamura (chief researcher), Kirin Holdings Company, Limited.). Then, genomic DNA was obtained using DNeasy. The structural gene of the genomic DNA was subjected to PCR (PCR conditions: 95° C. for 5 minutes; 30 cycles of 95° C. for 30 seconds, 55° C. for 30 seconds, and 72° C. for 5 minutes; and 72° C. for 10 minutes) using primers (U883: AGCAATCAAACATGGGTATTG (SEQ ID NO: 27); and U876: TGATGTGAACTTGAGATTGGTG (SEQ ID NO: 28)). Thus, the gene region was obtained. In addition, cloning was carried out using a TOPOTA cloning kit for sequencing. Further, the nucleotide sequence was determined using ABI310. As a result, it was found that a line having a mutated gene was not included among 10 stocks provided herein. However, it is possible to obtain a plant having a mutated gene by repeatedly carrying out the above procedures using a plant subjected to sufficient mutation treatment.

All publications, patents, and patent applications cited herein are incorporated herein by reference in their entirety.

INDUSTRIAL APPLICABILITY

The glycoalkaloid biosynthetic enzyme and the organism production/detection method using the gene of the present invention are useful for the development of production of glycoalkaloid compounds using organisms such as plants and selection of solanaceous plant varieties such as potatoes.

FREE TEXT OF SEQUENCE LISTINGS

Primers: SEQ ID NOS: 6 to 17 and 23 to 28

The invention claimed is:

1. A method for crossing a plant having at least one polymorphism or mutation in the coding region of a plant glycoalkaloid gene selected from the group consisting of SEQ ID NOs: 2, 4, 19 and 21, comprising:
   (i) isolating a nucleic acid from a tomato or potato plant, wherein said nucleic acid is a genomic DNA containing said plant gene, or an RNA expressed from said plant gene;
   (ii) amplifying a polynucleotide sequence containing said plant gene from said nucleic acid, when said nucleic acid is genomic DNA; or when said nucleic acid is RNA, synthesizing cDNA via reverse transcription from said RNA, and amplifying a polynucleotide sequence corresponding to said plant gene from said cDNA;
   (iii) determining whether said amplified sequence contains any mutations and/or polymorphisms in the coding sequence as compared to a corresponding reference coding sequence selected from the group consisting of SEQ ID NOs: 2, 4, 19 and 21, to determine the existence of a mutation and/or polymorphism in said plant gene;
   (iv) selecting a tomato or potato plant comprising the at least one polymorphism or mutation and also having altered expression of said plant glycoalkaloid gene or altered activity of the enzyme encoded by said plant glycoalkaloid gene; and
   (v) crossing said tomato or potato plant with a different tomato or potato plant, wherein the ability to express a glycoalkaloid biosynthetic enzyme gene or the glycoalkaloid biosynthetic enzyme activity has been modified in a tomato or potato plant made by said cross when compared to a plant not having said at least on polymorphism or mutation.

2. A method for altering the expression of a glycoalkaloid biosynthetic enzyme gene or the activity of a glycoalkaloid biosynthetic enzyme encoded by a plant gene selected from the group consisting of SEQ ID NOs: 2, 4, 19 and 21, comprising:
   (i) obtaining a plant from a mutagenized population of a tomato or potato plant variety;
   (ii) isolating a nucleic acid from said tomato or potato plant, wherein said nucleic acid is a genomic DNA containing said plant gene, or an RNA expressed from said plant gene;
   (iii) amplifying a polynucleotide sequence containing said plant gene from said nucleic acid, when said nucleic acid is genomic DNA; or when said nucleic acid is RNA, synthesizing cDNA via reverse transcription from said RNA, and amplifying a polynucleotide sequence corresponding to said plant gene from said cDNA;
   (iv) determining whether said amplified polynucleotide sequence contains any mutations in the coding sequence as compared to a corresponding reference coding sequence selected from the group consisting of SEQ ID NOs: 2, 4, 19 and 21, to determine the existence of at least one mutation in said plant gene; and
   (v) selecting a tomato or potato plant comprising the at least one mutation and which also has altered expression of said plant glycoalkaloid gene or altered activity of the enzyme encoded by said plant glycoalkaloid gene when compared to a tomato or potato plant not having said at least one mutation; wherein said mutagenized population was generated by artificial mutagenesis or transformation.

3. A plant selected by the method according to claim 2.

4. A method for crossing a plant having at least one polymorphism or mutation in a potato plant glycoalkaloid gene selected from the group consisting of SEQ ID NO: 5 or 22 comprising:
   (i) isolating a nucleic acid from a potato plant, wherein said nucleic acid is a genomic DNA containing said plant gene;
   (ii) amplifying a polynucleotide sequence containing said plant gene from said nucleic acid;
   (iii) determining whether said amplified sequence contains any mutations and/or polymorphisms as compared to a corresponding reference sequence selected from the group consisting of SEQ ID NO: 5 and 22, to determine the existence of a mutation and/or polymorphism in said plant gene;
   (iv) selecting a potato plant comprising the at least one polymorphism or mutation and also having altered expression of said plant glycoalkaloid gene or altered activity of the enzyme encoded by said plant glycoalkaloid gene; and
   (v) crossing said potato plant with a different potato plant, wherein the ability to express a glycoalkaloid biosynthetic enzyme gene or the glycoalkaloid biosynthetic enzyme activity has been modified in a potato plant made by said cross when compared to a plant not having said at least one polymorphism or mutation.

5. A method for altering the expression of a glycoalkaloid biosynthetic enzyme gene or the activity of a glycoalkaloid biosynthetic enzyme encoded by a potato plant glycoalkaloid gene selected from the group consisting of SEQ ID NO: 5 or 22 comprising:
   (i) obtaining a plant from a mutagenized population of a potato plant variety;
   (ii) isolating a nucleic acid from said plant, wherein said nucleic acid is a genomic DNA containing said plant gene, or an RNA expressed from said plant gene;
   (iii) amplifying a polynucleotide sequence containing said plant gene from said nucleic acid, when said nucleic acid is genomic DNA; or when said nucleic acid is RNA, synthesizing cDNA via reverse transcription from said RNA, and amplifying a polynucleotide sequence corresponding to said plant gene from said cDNA;
   (iv) determining whether said amplified polynucleotide sequence contains any mutations as compared to a corresponding reference sequence selected from the group consisting of SEQ ID NO: 5 or 22, to determine the existence of at least one mutation in said plant gene; and (v) selecting a potato plant comprising the at least one mutation and which also has altered expression of said plant glycoalkaloid gene or altered activity of the enzyme encoded by said plant glycoalkaloid gene when compared to a potato plant not having said at least one mutation; wherein said mutagenized population was generated by artificial mutagenesis or transformation.

6. A mutant plant selected by the method according to claim 5.

* * * * *

```
                    SEQUENCE LISTING

<160> NUMBER OF SEQ ID NOS: 28

<210> SEQ ID NO 1
<211> LENGTH: 498
<212> TYPE: PRT
<213> ORGANISM: Solanum tuberosum

<400> SEQUENCE: 1

Met Ala Ile Ala Thr Val Ile Gly Ala Thr Ile Gly Ile Leu Ile Ala
1               5                   10                  15

Ile Phe Cys Val Lys Ser Phe Tyr Thr Leu Trp Trp Trp Pro Lys Met
                20                  25                  30

Ile Glu Lys Lys Leu Lys Lys Glu Gly Ile His Gly Leu Pro Tyr Gln
            35                  40                  45

Phe Leu Phe Gly Asn Leu Lys Glu Met Thr Arg Met Ser Arg Glu Ala
        50                  55                  60

Lys Lys Thr Pro Leu Val Asn His Asp Ile Val Pro Trp Val Asn Pro
65                  70                  75                  80

Phe Ile Leu His Leu Ser Lys Thr Tyr Glu Arg Leu Phe Val Met Trp
                85                  90                  95

Ala Gly Pro Thr Pro Arg Ile Val Val Ser Asp Pro Lys Leu Ile Lys
                100                 105                 110

Glu Val Val Asn Arg His Asn Glu Phe Gln Lys Pro Gln Ala Asn Ala
            115                 120                 125

Phe Ile Asp Met Phe Val Thr Gly Leu Ala Ser Tyr Asn Gly Gln Lys
        130                 135                 140

Trp Asp His His Arg Lys Ile Leu Asn Pro Ala Phe His Ile Glu Lys
145                 150                 155                 160

Ile Lys Arg Leu Tyr Pro Ala Phe Cys Glu Cys Asp Glu Met Ile
                165                 170                 175

Asn Arg Trp Glu Glu Leu Val Ser Lys Ser Gly Ser Cys Glu Leu Asp
            180                 185                 190

Val Ala Asp Glu Phe Leu Asn Val Gly Gly Asp Val Ile Ser Arg Ala
        195                 200                 205

Ala Phe Gly Ser Asn Ile Glu Glu Gly Arg Thr Ile Phe Ile Leu Gln
        210                 215                 220

Lys Glu Gln Cys Asp Leu Ile Leu Ala Ser Pro Phe Thr Leu Phe Phe
225                 230                 235                 240

Pro Leu Leu Arg Phe Phe Pro Thr Ala Ser Asn Arg Ala Arg Tyr
                245                 250                 255

Ile Tyr Lys Lys Val Leu Ser Leu Ile Asn Gly Ile Ile Glu Lys Lys
                260                 265                 270

Lys Asp Thr Met Arg Arg Gly Val Ser Gln Ser Asp Ile Leu Gly
            275                 280                 285

Leu Leu Leu Lys Gly Gly Leu Ser Thr Thr Glu Ile Ile Glu Glu Cys
        290                 295                 300

Lys Glu Phe Tyr Leu Ala Gly Gln Asp Thr Thr Ala Leu Leu Ser
305                 310                 315                 320

Trp Thr Leu Val Ala Leu Ser Met His Pro Glu Trp Gln Asp Lys Ala
                325                 330                 335
```

```
Arg Asn Glu Val Phe Gln Val Leu Gly Lys Asn Lys Pro Lys Phe Glu
            340                 345                 350

Asp Leu Asn Gln Leu Lys Ile Met Asn Met Ile Phe Gln Glu Val Leu
            355                 360                 365

Arg Leu Tyr Pro Ala Leu Thr Leu Met Arg Ser Thr Val Lys Asn Thr
        370                 375                 380

Lys Leu Gly Asp Met Thr Ile Pro Ala Gly Val Gln Ile Phe Val Pro
385                 390                 395                 400

Ile Tyr Ile Ala His Arg Asp Pro Gln Val Trp Gly Asp Asp Ala Leu
                405                 410                 415

Ile Phe Asn Pro Asn Arg Phe Ser Glu Gly Val Ser Lys Ala Ala Lys
                420                 425                 430

Glu Pro Leu Tyr Phe Pro Phe Gly Trp Gly Pro Arg Met Cys Ile Gly
            435                 440                 445

Asn Asn Phe Gly Met Ala Glu Ala Lys Leu Val Leu Ser Gln Ile Leu
        450                 455                 460

Gln Arg Phe Trp Phe Lys Leu Ser Pro Ser Tyr Val His Ala Pro Gln
465                 470                 475                 480

Ala Ile Leu Val Met Lys Pro Gln Tyr Gly Ala Gln Ile Ile Leu Asn
                485                 490                 495

Lys Leu

<210> SEQ ID NO 2
<211> LENGTH: 1494
<212> TYPE: DNA
<213> ORGANISM: Solanum tuberosum

<400> SEQUENCE: 2
atggcaattg caacagtaat tggtgcaaca attggtattt tgatagcgat ttttgtgta       60 aaatcgtttt acacattatg gtggtggcca aagatgatcg aaagaagct gaagaaggaa      120 ggtattcatg ggctgcccta ccaatttctg tttggaaatc tgaaagagat gacgagaatg      180
tctagagaag caaagaaaac accgttagta aatcatgata tcgttccttg ggttaatcct      240
tttattcttc atctttctaa aacttacgag agattatttg tgatgtgggc tggaccaaca      300
cctcggattg tagtatcaga tccaaagcta attaagaag tggtgaacag acataatgaa      360
tttcagaagc tcaagccaa tgcgttcatt gacatgtttg ttactggact tgctagttac      420
aatggtcaaa atgggaccac catagaaag tactaaaacc ctgcttttca tatagagaag      480
attaagaggt tgtacccagc attttgtgag tgttgtgatg aaatgataaa tagatgggag      540
gaattggtta gcaaaagtgg aagttgtgag ttggatgtgg cagatgaatt cctaaatgta      600
ggtggagatg ttatatctag agctgctttt ggtagcaata ttgaagaagg aaggactatt      660
ttcatacttc agaaagagca gtgcgatctt attttggctt ctccatttac tcttttcttt      720
cccttactaa gattctttcc aacagcatca aacagaagag caagatacat ctacaagaaa      780
gtgttatcat tgattaacgg aataatagag aagaaaaaag acactatgcg aagaggagtc      840
tcacaaagtg atgatatttt agggttactc ttaaaggag gactatcaac cactgaaata      900
attgaagaat gtaaggaatt ctatcttgca ggacaagata caaccacagc tttgctctct      960
tggacattgg ttgccttgag tatgcaccct gagtggcaag acaaagctag aatgaagtc      1020 tttcaagtcc ttgaaaaaaa caaaccaaag tttgaggact tgaatcaatt aaaaataatg      1080
aacatgatct ccaagaggt gttgagatta tatccagcac tcacccttat gcgaagcacc      1140
```

```
gtaaagaaca ctaaattggg agatatgaca attcctgcag gagtacaaat atttgtgcct   1200
atatatatag cacatcgcga tccccaagta tggggagacg atgcattgat attcaatcca   1260
aataggttct cagaaggggt atccaaagct gcaaagagcc cttgtatttt ccccttggt   1320 tggggtcctc gaatgtgcat tggtaataac tttggcatgg cagaagccaa gctcgtttta   1380
tctcaaattc tgcagcgttt ttggtttaag ctctctcctt cctatgttca tgcccctcag   1440
gcaatactcg ttatgaagcc tcagtatggt gctcagataa tcctcaacaa gctt         1494
```

<210> SEQ ID NO 3
<211> LENGTH: 498
<212> TYPE: PRT
<213> ORGANISM: Solanum lycopersicum

<400> SEQUENCE: 3

```
Met Ala Ile Val Thr Val Ile Gly Ala Thr Gly Ile Leu Ile Ala
1               5                   10                  15

Leu Phe Phe Val Lys Ser Phe Tyr Thr Leu Trp Trp Pro Lys Met
            20                  25                  30

Ile Glu Lys Lys Leu Lys Lys Glu Gly Ile His Gly Gln Pro Tyr Gln
        35                  40                  45

Phe Leu Phe Gly Asn Leu Lys Glu Met Thr Arg Met Ser Arg Glu Ala
    50                  55                  60

Lys Lys Lys Pro Leu Val Asn His Asp Ile Val Pro Trp Val Asn Pro
65                  70                  75                  80

Phe Ile Leu His Leu Ser Lys Thr Tyr Glu Arg Leu Phe Val Met Trp
                85                  90                  95

Ala Gly Pro Thr Pro Arg Ile Thr Val Thr Asp Pro Lys Leu Ile Lys
            100                 105                 110

Glu Val Val Asn Arg His Asn Glu Phe Gln Lys Pro Gln Ala Asn Ala
        115                 120                 125

Phe Ile Asp Met Phe Val Thr Gly Leu Ala Ser Tyr Asn Gly Gln Lys
    130                 135                 140

Trp Asp His His Arg Lys Ile Leu Asn Pro Ala Phe His Ile Glu Lys
145                 150                 155                 160

Ile Lys Arg Leu Tyr Pro Ala Phe Cys Glu Cys Cys Asp Glu Met Ile
                165                 170                 175

Asn Arg Trp Glu Asp Leu Val Ser Lys Thr Gly Ser Cys Glu Leu Asp
            180                 185                 190

Val Ala Asp Glu Phe Leu Asn Val Gly Gly Asp Val Ile Ser Arg Ala
        195                 200                 205

Ala Phe Gly Ser Asn Ile Glu Glu Gly Arg Thr Ile Phe Ile Leu Gln
    210                 215                 220

Lys Glu Gln Cys Asp Leu Ile Leu Ala Ser Pro Phe Thr Leu Phe Phe
225                 230                 235                 240

Pro Leu Leu Arg Phe Phe Pro Thr Glu Ser Asn Arg Arg Ala Arg Tyr
                245                 250                 255

Ile Tyr Lys Lys Val Leu Ser Leu Ile Lys Gly Ile Ile Glu Lys Lys
            260                 265                 270

Glu Asp Ala Met Arg Arg Gly Val Ser Glu Ser Asp Ile Leu Gly
        275                 280                 285

Leu Leu Leu Lys Gly Gly Leu Ser Thr Thr Glu Ile Ile Glu Glu Cys
    290                 295                 300

Lys Glu Phe Tyr Leu Ala Gly Gln Asp Thr Thr Thr Ala Leu Leu Ser
305                 310                 315                 320
```

```
Trp Thr Leu Val Ala Leu Ser Met His Pro Glu Trp Gln Asp Lys Ala
                325                 330                 335

Arg Asn Glu Val Phe Gln Val Leu Gly Lys Asn Lys Pro Lys Phe Glu
            340                 345                 350

Asp Leu Asn Gln Leu Lys Ile Met Asn Met Ile Phe Gln Glu Val Leu
        355                 360                 365

Arg Leu Tyr Pro Ala Leu Thr Leu Met Arg Ser Thr Ser Lys Asp Thr
    370                 375                 380

Lys Leu Gly Glu Met Thr Ile Pro Ala Gly Val Gln Ile Phe Val Pro
385                 390                 395                 400

Ile Tyr Ile Ala His Arg Asp Pro Gln Val Trp Gly Asp Asp Ala Leu
                405                 410                 415

Ile Phe Asn Pro Asn Arg Phe Ser Glu Gly Val Ser Lys Ala Ala Lys
            420                 425                 430

Glu Pro Leu Tyr Phe Pro Phe Gly Trp Gly Pro Arg Met Cys Ile Gly
        435                 440                 445

Asn Asn Phe Gly Met Ala Glu Ala Lys Leu Val Leu Ser Gln Ile Leu
    450                 455                 460

Gln Arg Phe Trp Phe Lys Leu Ser Pro Ser Tyr Val His Ala Pro Gln
465                 470                 475                 480

Ala Ile Leu Val Met Lys Pro Gln Tyr Gly Ala Gln Ile Ile Leu Asn
                485                 490                 495

Lys Leu

<210> SEQ ID NO 4
<211> LENGTH: 1494
<212> TYPE: DNA
<213> ORGANISM: Solanum lycopersicum

<400> SEQUENCE: 4
atggcaattg ttacagtaat tggtgcaacg attggcattt tgatagccct attttttgta      60
aaatcgtttt tacattatg gtggtggcca agatgatcg aaaagaagct gaagaaggaa       120
ggtattcatg gtcagccgta ccaatttctg tttggaaatc tgaaagagat gacgagaatg     180
tctagagaag caaagaaaaa accattagta aatcacgata ttgttccttg ggtgaatcct    240
tttattcttc atctttctaa aacttacgag agattatttg tgatgtgggc tggaccaacc    300
cctcggatta cagtaacaga tccaaagcta ataaagaag tggtgaacag acataatgaa     360
tttcaaaagc tcaagccaa tgccttcatt gatatgtttg ttactggact tgctagttac    420
aatggtcaaa atgggatca ccatagaaag atactaaacc cggcttttca tatagagaag    480
attaagaggt tgtacccagc attttgcgag tgttgtgatg aaatgataaa tagatgggag    540
gacttggtta gcaaaactgg aagttgtgaa ttggatgtag cagatgaatt tctaaatgta   600
ggtggagatg ttatatcgag agctgctttt ggtagcaata ttgaagaagg aaggactatt    660
ttcatacttc agaaagagca gtgcgatctt attttggctt ctccatttac tctcttcttt    720
cccttactaa gattctttcc aacagaatca acagaagag caagatacat ctacaaaaaa    780
gtgttatcat tgatcaaagg aatcatagag aagaaagaag acgctatgcg aagaggagtc    840
tcagaaagtg atgatatatt aggattactc ttaaaggag gactgtcaac cactgaaata    900
attgaagaat gtaaggaatt ctatcttgca ggacaagata caaccacagc tttgctctcc    960
tggacattgg tagccttgag tatgcatcct gagtggcaag acaaagctag aaatgaagta  1020
tttcaagtac ttggaaaaaa caaaccaaag tttgaggact tgaatcaatt aaaaataatg  1080
```

```
aacatgatct tccaagaggt gttgagatta tacccagcac tcacccttat gcgaagcacc    1140
tcaaaggaca ctaaattggg agaaatgaca attcctgcag gagtacaaat ttttgtgcct    1200
atatacatag cacatcgcga cccccaagta tggggagacg atgcactgat tttcaatcca    1260
aataggttct cagaaggggt atccaaagct gcaaagagc cattgtattt cccttcggt      1320 tggggtcctc gaatgtgcat tggtaataac tttggaatgg cagaagcaaa gctcgtttta    1380
tctcaaattc tgcagaggtt ttggttcaag ctctctcctt cctatgttca tgcccctcag    1440
gcaatactcg ttatgaagcc tcagtatggt gctcagataa tcctcaacaa gctc          1494
```

<210> SEQ ID NO 5
<211> LENGTH: 1974
<212> TYPE: DNA
<213> ORGANISM: Solanum tuberosum

<400> SEQUENCE: 5

```
gcttgctctg ttcttgtaca tctcaacctc actattcatt catcagttga tagaaaatat      60
ctaggctatg gcaattgcaa cagtaattgg tgcaacaatt ggtattttga tagcgatttt     120
ttgtgtaaaa tcgttttaca cattatggtg gtggccaaag atgatcgaaa agaagctgaa     180
gaaggaaggt attcatgggc tgccctacca atttctgttt ggaaatctga agagatgac      240 gagaatgtct agagaagcaa agaaaacacc gttagtaaat catgatatcg ttccttgggt     300
taatcctttt attcttcatc tttctaaaac ttacggtaag ccagccatgt atatttcttt     360
aaaacacatt ccatatatat tttgttaaaa ctttacctaa ttaggtatgg tgcagagaga    420
ttatttgtga tgtgggctgg accaacaccct cggattgtag tatcagatcc aaagctaatt    480
aaagaagtgg tgaacagaca taatgaattt cagaagcctc aagccaatgc gttcattgac     540
atgtttgtta ctggacttgc tagttacaat ggtcaaaaat gggaccacca tagaaagata     600
ctaaaccctg cttttcatat agagaagatt aaggtattga actagttatt cctctcttct     660
ttttggatga ccattcattt tcctattttt gtgtgactgc acagaggttg tacccagcat     720
tttgtgagtg ttgtgatgaa atgataaata gatgggagga attggttagc aaaagtggaa     780
gttgtgagtt ggatgtggca gatgaattcc taaatgtagg tggagatgtt atatctagag     840
ctgcttttgg tagcaatatt gaagaaggaa ggactatttt catacttcag aaagagcagt     900
gcgatcttat tttggcttct ccatttactc ttttctttcc cttactaagg tgagtattta     960
tctaatttct tcaaaaatat atatatgtat tgttataact aacatacatt ttaactacgc    1020
agattctttc caacagcatc aaacagaaga gcaagataca tctacaagaa agtgttatca    1080
ttgattaacg gaataataga gaagaaaaaa gacactatgc gaagaggagt ctcacaaagt    1140
gatgatattt tagggttact cttaaaagga ggactatcaa ccactgaaat aattgaagaa    1200
tgtaaggaat tctatcttgc aggacaagat acaaccacag cttttgctctc ttggacattg   1260 gttgccttga gtatgcaccc tgagtggcaa gacaaagcta gaaatgaagt cttttcaagtc   1320 cttggaaaaa acaaaccaaa gtttgaggac ttgaatcaat taaaaatagt aagctctctc    1380
tttagtcttt atgatgatac agagtcctaa tttttactact gagtactact ataaacatgt   1440
cattaatatt tgtgtattaa tactagatga acatgatctt ccaagaggtg ttgagattat    1500
atccagcact caccccttatg cgaagcaccg taaagaacac taaattggga gatatgacaa    1560
ttcctgcagg agtacaaata tttgtgccta tatatatage acatcgcgat ccccaagtat    1620
ggggagacga tgcattgata ttcaatccaa ataggttctc agaaggggta tccaaagctg    1680
```
caaaagagcc cttgtatttc cccttttggtt ggggtcctcg aatgtgcatt ggtaataact    1740
ttggcatggc agaagccaag ctcgttttat ctcaaattct gcagcgtttt tggtttaagc    1800
tctctccttc ctatgttcat gccctcagg caatactcgt tatgaagcct cagtatggtg    1860
ctcagataat cctcaacaag ctttgacctt tcgggctggt agttaattat aagtggtact    1920
agttctttca ataaatcagg ttgagttgta ttctgctgct aattctgctt ttca    1974

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 6
gcttgctctg ttcttgtaca tctc    24

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 7
tgaaaagcag aattagcagc a    21

<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 8
gagctctaga gaagcaaaga aaacacc    27

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 9
ggatccatat gctaaccaat tcctcccatc    30

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 10
taaagcacga ggaagcggt    19

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 11

-continued

```
gcacaacaga caatcggct                                          19

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 12
gagctctaga gaagcaaaga aaacacc                                 27

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
gggcatgaac ataggaagga                                         20

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 14
taaagcacga ggaagcggt                                          19

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 15
gcacaacaga caatcggct                                          19

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 16
gcttgctctg ttcttgtaca tctc                                    24

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 17
tgaaaagcag aattagcagc a                                       21

<210> SEQ ID NO 18
<211> LENGTH: 517
<212> TYPE: PRT
```

<213> ORGANISM: Solanum tuberosum

<400> SEQUENCE: 18

```
Met Gly Ile Ala Val Phe Ile Ala Leu Ala Val Cys Leu Pro Phe Ser
1               5                   10                  15

Phe Trp Cys Leu Lys Leu Leu Tyr Phe Val Trp Arg Pro Lys Thr
            20                  25                  30

Val Glu Asn Glu Leu Arg Gln Gln Gly Ile Tyr Gly Arg Pro Tyr Arg
                35                  40                  45

Phe Leu Phe Gly Asn Leu Lys Glu Met Ile Glu Met Asn Lys Ile Ala
            50                  55                  60

Lys Ser Lys Pro Met Pro Leu His His Asp Phe Thr Pro Arg Leu Asn
65                  70                  75                  80

Pro Leu Phe Tyr Glu Leu Ala Thr Thr Tyr Lys Lys Leu Tyr Leu Phe
                85                  90                  95

Trp Leu Gly Pro Ile Pro Arg Leu Thr Ile Leu Asp Pro Lys Leu Ile
            100                 105                 110

Lys Glu Val Leu Ser Asn Lys Ser Gly Glu Phe Arg Lys Pro Asn Ile
            115                 120                 125

Ser Ala Phe Leu Lys Leu Phe Val Thr Gly Leu Gly Thr Tyr Asp Gly
130                 135                 140

Glu Lys Trp Ala Lys His Arg Lys Ile Leu Asn Pro Ala Phe His Met
145                 150                 155                 160

Glu Lys Leu Lys Val Met Leu Gly Leu Phe Val Asn Cys Thr Asp Asp
                165                 170                 175

Met Ile Ser Arg Trp Asp Lys Leu Thr Gly Ser Thr Gly Gly Ser Cys
            180                 185                 190

Glu Val Asp Ile Ser Gln Glu Phe His Asn Leu Thr Gly Asp Met Leu
            195                 200                 205

Ser Lys Ala Ala Phe Gly Ser Asn Phe Glu Glu Gly Lys Leu Val Phe
210                 215                 220

Ser Leu Leu Arg Glu Gln Cys Glu Leu Ile Phe Thr Ala Lys Leu Ala
225                 230                 235                 240

Ile Asn Val Phe Pro Trp Leu Arg Phe Val Pro Thr Lys Thr Asn Arg
                245                 250                 255

Arg Arg Leu Tyr Ile Tyr Asn Thr Val Arg Ser Ser Leu Lys Ala Ile
            260                 265                 270

Ile Glu Lys Arg Glu Lys Glu Val Gln Ser Gly Lys Ser His Asn Glu
            275                 280                 285

Asp Leu Leu Gly Leu Leu Met Lys Ser Asn Gln Glu Gln Gln Gly
            290                 295                 300

Asn Lys Asn Ser Asn Lys Gly Met Ser Thr Glu Asp Met Ile Glu Glu
305                 310                 315                 320

Cys Asn Ser Phe Tyr Phe Ala Gly Gln Glu Thr Thr Ala Thr Leu Leu
                325                 330                 335

Thr Trp Thr Ala Ile Val Leu Thr Met His Pro Asp Trp Gln Glu Lys
            340                 345                 350

Ala Arg Lys Glu Val Leu Glu Val Ile Gly Lys Asp Glu Pro Lys Phe
            355                 360                 365

Asp Gln Leu Asn His Leu Lys Ile Val Thr Met Ile Leu His Glu Val
        370                 375                 380

Leu Arg Leu Tyr Pro Ser Gly Ser Leu Val Arg Glu Thr Asn Lys Lys
385                 390                 395                 400
```

```
Thr Lys Leu Gly Glu Tyr Thr Ile Pro Ala Gly Gln Leu Leu Val
                405                 410                 415

Pro Leu Gln Thr Ile His Arg Asp Thr Glu Ala Trp Gly Glu Asp Ala
            420                 425                 430

Leu Ile Phe Asn Pro Glu Arg Phe Ser Glu Gly Val Ser Lys Ala Ser
                435                 440                 445

Lys Asp Leu Met Tyr Phe Pro Phe Gly Trp Gly Ser Arg Ile Cys Leu
            450                 455                 460

Gly Met Asn Val Ser Met Ile Gln Gly Lys Leu Val Leu Ala Lys Ile
465                 470                 475                 480

Leu Gln Asn Tyr Ser Phe Glu Leu Ser Pro Ser Tyr Ala His Gly Pro
                485                 490                 495

Thr Met Pro Ala Leu Val Leu Gln Pro Gln Tyr Gly Ala Pro Met Ile
            500                 505                 510

Leu Arg Lys Leu Ser
            515

<210> SEQ ID NO 19
<211> LENGTH: 1551
<212> TYPE: DNA
<213> ORGANISM: Solanum tuberosum

<400> SEQUENCE: 19
atgggtattg cagttttcat tgctttggcc gtatgtttgc ctttcagttt ttggtgccta      60
aaattgctct actttgtatg gtggcgtccc aaaacagtag aaaatgaact gcggcagcaa     120
ggaatatatg ggcgtcccta tagattctta tttggaaatc taaggagat gatagagatg     180 aataaaatag ccaagtctaa acccatgcca ttgcaccacg atttcacacc tcgacttaat     240
ccattgttct atgaactggc caccacttac aagaaacttt acttgttttg ctaggaccg      300 atacctcgat taaccatttt ggatcccaag ttaattaagg aagtactgtc aaacaaatcg     360
ggtgagttca gaaaccaaa catcagcgct ttcctgaagc tatttgtaac ggggctgggg      420
acttacgatg gtgaaaaatg ggcgaaacac agaaaaattc ttaatccggc tttccacatg     480
gaaaaattga aggtgatgtt gggattattt gttaactgta ccgatgacat gataagcaga     540
tgggacaagc taactggttc aacgggtggt tcttgtgaag tagatatttc tcaagaattt     600
cataatttaa ctggagatat gctatcgaaa gcagccttcg gtagcaattt tgaagaaggg     660
aagttggtat tttcacttct gagagagcaa tgtgaactaa ttttcactgc aaagcttgct     720
attaatgtct tcccatggtt aaggtttgtg ccaacgaaaa ctaataggag aagattgtac     780
atctataaca cagttcgtag ttcgctaaaa gcaataattg agaaacgaga gaagaggta     840 caatctggaa aatcacacaa tgaagatctg ttgggttttgc taatgaaatc taatcaggaa     900
gaacagcaag ggaataagaa ctcgaacaaa ggaatgagta cagaggatat gatagaagag     960
tgcaactctt tctattttgc tggtcaagag actactgcaa ctttgttaac atggactgca    1020
attgtcttga ctatgcatcc agattggcaa gagaaagcca ggaagaagt tcttgaagtc    1080 attggaaaag atgagcctaa gtttgatcaa ctcaaccatc taaagattgt aactatgatc    1140
ttgcacgagg ttctgaggtt atatccatca ggttctcttg ttagagaaac aaacaaaaag    1200
acaaagcttg gagagtatac aatcccagca ggtgcgcaac ttttagttcc tctacaaaca    1260
atccatcgcg atacagaggc atggggagaa gatgctctaa ttttcaatcc agaaaggttt    1320
tcagaagggg tatcaaaagc atcaaggac ctgatgtact ttccgtttgg ttggggttct    1380
cggatatgcc ttggaatgaa tgtttccatg attcaaggga agcttgtttt ggctaaaatc    1440
```

```
ttacagaact actcctttga gctttccccc tcctatgctc atggtccaac catgccagct    1500
cttgttctac aaccacaata tggtgctcct atgatccttc gaaagctatc a             1551
```

<210> SEQ ID NO 20
<211> LENGTH: 516
<212> TYPE: PRT
<213> ORGANISM: Solanum lycopersicum

<400> SEQUENCE: 20

```
Met Ala Ile Ala Ile Phe Ile Ala Leu Ala Ile Phe Phe Pro Phe Thr
1               5                   10                  15

Phe Trp Cys Leu Lys Leu Leu Tyr Phe Val Trp Arg Pro Lys Thr
            20                  25                  30

Val Glu Asn Glu Leu Arg His Gln Gly Ile Tyr Gly Arg Pro Tyr Arg
        35                  40                  45

Phe Leu Phe Gly Asn Leu Lys Glu Met Ile Glu Met Asn Lys Ile Ala
    50                  55                  60

Lys Ser Lys Pro Met Pro Leu His His Asp Phe Thr Pro Arg Leu Asn
65                  70                  75                  80

Pro Leu Phe Tyr Glu Leu Ala Thr Thr Tyr Lys Lys Leu Tyr Leu Phe
                85                  90                  95

Trp Leu Gly Pro Ile Pro Arg Leu Thr Ile Leu Asp Pro Lys Leu Ile
            100                 105                 110

Lys Glu Val Leu Ser Asn Lys Ser Gly Glu Phe Arg Lys Pro Lys Ile
        115                 120                 125

Ser Ala Phe Leu Lys Leu Phe Val Thr Gly Leu Gly Thr Tyr Asp Gly
    130                 135                 140

Glu Lys Trp Ala Lys His Arg Lys Ile Leu Asn Pro Ala Phe His Met
145                 150                 155                 160

Glu Lys Leu Lys Val Met Leu Gly Leu Phe Val Glu Cys Thr Asp Asp
                165                 170                 175

Met Ile Ser Arg Trp Asp Lys Leu Thr Gly Ser Thr Gly Ser Cys Glu
            180                 185                 190

Leu Asp Ile Ser Gln Glu Phe His Asn Leu Thr Gly Asp Met Leu Ser
        195                 200                 205

Lys Ala Ala Phe Gly Ser Asn Phe Glu Glu Gly Lys Leu Val Phe Ser
    210                 215                 220

Leu Leu Arg Glu Gln Cys Glu Leu Ile Phe Thr Ala Lys Leu Ala Ile
225                 230                 235                 240

Asn Val Phe Pro Trp Leu Arg Phe Val Pro Thr Lys Thr Asn Arg Arg
                245                 250                 255

Arg Leu Tyr Ile Tyr Asn Thr Val Arg Ser Ser Leu Lys Ser Ile Ile
            260                 265                 270

Glu Lys Arg Glu Lys Glu Val Gln Ser Gly Lys Ser His Asn Glu Asp
        275                 280                 285

Leu Leu Gly Leu Leu Met Lys Ser Asn Gln Glu Gln Gln Gly Asn
    290                 295                 300

Lys Asn Ser Asn Lys Gly Met Ser Thr Glu Asp Met Ile Glu Glu Cys
305                 310                 315                 320

Asn Ser Phe Tyr Phe Ala Gly Gln Glu Thr Thr Ala Thr Leu Leu Thr
                325                 330                 335

Trp Thr Ala Ile Val Leu Thr Met His Pro Asp Trp Gln Glu Lys Ala
            340                 345                 350
```

Arg Lys Glu Val Leu Gln Val Ile Gly Lys Asp Glu Pro Lys Phe Asp
            355                 360                 365

Gln Leu Asn His Leu Lys Ile Val Thr Met Ile Leu His Glu Val Leu
        370                 375                 380

Arg Leu Tyr Pro Ser Gly Ser Leu Val Arg Glu Thr Asn Lys Lys Thr
385                 390                 395                 400

Lys Leu Gly Gly Tyr Thr Ile Pro Ala Gly Ala Gln Leu Leu Val Pro
                405                 410                 415

Leu Gln Thr Ile His Arg Asp Thr Glu Ala Trp Gly Glu Asp Ala Leu
            420                 425                 430

Ile Phe Asn Pro Glu Arg Phe Ser Glu Gly Val Ser Lys Ala Ser Lys
        435                 440                 445

Asp Leu Met Tyr Phe Pro Phe Gly Trp Gly Ser Arg Ile Cys Leu Gly
    450                 455                 460

Met Asn Val Ser Met Ile Gln Gly Lys Leu Val Leu Ala Lys Ile Leu
465                 470                 475                 480

Gln Asn Tyr Ser Phe Glu Leu Ser Pro Ser Tyr Ala His Gly Pro Thr
                485                 490                 495

Met Pro Ala Leu Val Leu Gln Pro Gln Tyr Gly Ala Pro Met Ile Val
            500                 505                 510

Arg Lys Leu Glu
        515

<210> SEQ ID NO 21
<211> LENGTH: 1548
<212> TYPE: DNA
<213> ORGANISM: Solanum lycopersicum

<400> SEQUENCE: 21

| atggctattg | caattttcat | agctttggcc | atatttttc | ctttcacttt | ttggtgccta | 60 |
| aaattgctct | actttgtatg | gtggcgtccg | aaaacagtag | aaaatgaact | gcgtcatcaa | 120 |
| ggaatctatg | ggcgtcccta | tagatttcta | tttggaaatc | taaaagagat | gatagagatg | 180 |
| aacaaaatag | ccaaatctaa | acccatgcca | ttgcaccacg | atttcacacc | tcgacttaat | 240 |
| ccattgttct | atgaactcgc | taccacttac | aagaaacttt | acttgttttg | ctaggaccc | 300 |
| atccctcgat | taaccatttt | ggatcccaag | ttaataaagg | aagtactgtc | aaacaaatct | 360 |
| ggtgagttca | gaaaccaaa | atcagtgct | tttctgaagc | tatttgtaac | agggctaggg | 420 |
| acttacgatg | gggaaaaatg | ggccaaacat | cgaaaaattc | ttaatccggc | attccacatg | 480 |
| gaaaaattga | aggtgatgct | gggattattt | gttgaatgca | cggatgacat | gataagcaga | 540 |
| tgggataagc | taacgggttc | aacgggttct | tgtgaattgg | atatttctca | agaatttcat | 600 |
| aatttaactg | gagatatgct | atcgaaagca | gctttcggta | gcaattttga | agaagggaaa | 660 |
| ttggtatttt | cacttctgag | agagcaatgt | gaactaattt | tcactgcaaa | gcttgctatt | 720 |
| aatgtcttcc | catggttaag | gtttgtgcca | acgaaaacta | ataggagaag | attgtacatc | 780 |
| tataacacag | ttcgtagttc | gttaaaatca | atcattgaga | acgagagaa | agaggtacaa | 840 |
| tctggaaaat | cacacaacga | agatctattg | ggtttgttga | tgaaatctaa | tcaggaagaa | 900 |
| cagcaaggga | ataagaactc | gaataaagga | atgagtacag | aggatatgat | agaagagtgt | 960 |
| aactctttct | actttgctgg | tcaagagact | actgcaactt | tgttaacatg | gactgcaatt | 1020 |
| gtgttgacta | tgcatccaga | ttggcaagag | aaagctagga | agaagttcct | tcaagtcatt | 1080 |
| ggaaaagatg | aacctaagtt | tgatcaactc | aaccacctaa | agattgtaac | aatgattttg | 1140 |

```
cacgaggttc tgaggctcta tccatcaggt tctctcgtta gagaaacaaa caaaaaaaca    1200
aagctcggag ggtatacaat cccagcaggt gcgcaacttt tagtgcctct acaaacaatt    1260
catcgggata cagaggcatg gggtgaagat gcattaattt tcaatccaga aaggttttca    1320
gaaggggtat caaaagcatc aaaggacctg atgtacttcc catttggttg gggttctcgg    1380
atatgccttg gaatgaatgt ttcgatgatt caagggaagc ttgttttggc taaaatctta    1440
cagaactact catttgagct ttccccatcc tatgctcatg tccaacaat gccagctctt     1500 gttctacaac cacaatatgg tgctcctatg attgttcgaa agctagaa                 1548
```

<210> SEQ ID NO 22
<211> LENGTH: 2102
<212> TYPE: DNA
<213> ORGANISM: Solanum tuberosum

<400> SEQUENCE: 22

```
agcaatcaaa catgggtatt gcagttttca ttgctttggc cgtatgtttg cctttcagtt      60
tttggtgcct aaaattgctc tactttgtat ggtggcgtcc caaaacagta gaaaatgaac     120
tgcggcagca aggaatatat gggcgtccct atagatttct atttggaaat ctaaaggaga    180
tgatagagat gaataaaata gccaagtcta aacccatgcc attgcaccac gatttcacac    240
ctcgacttaa tccattgttc tatgaactgg ccaccactta cagtaattat tcttttctaat   300 ttccaatggc cttgttacag taacattttt aatttgaaca ctgattgtgg agtggttatt    360
attgcagaga aactttactt gttttggcta ggaccgatac ctcgattaac cattttggat    420
cccaagttaa ttaaggaagt actgtcaaac aaatcgggtg agttcagaaa accaaacatc   480
agcgctttcc tgaagctatt tgtaacgggg ctggggactt acgatggtga aaaatgggcg    540
aaacacagaa aaattcttaa tccggctttc cacatggaaa aattgaaggt atttactagt    600
attagttttc tggtatacaa tttccttaag tgatttatta ttataattgt tggtgtttgc    660
acaggtgatg ttgggattat ttgttaactg taccgatgac atgataagca gatgggacaa    720
gctaactggt tcaacgggtg gttcttgtga agtagatatt tctcaagaat tcataatttt    780
aactggagat atgctatcga aagcagcctt cggtagcaat tttgaagaag ggaagttggt    840
attttcactt ctgagagagc aatgtgaact aattttcact gcaaagcttg ctattaatgt    900
cttcccatgg ttaaggtact tgtagtaatt aactaatgcc ttcgttttcc ttgcattgga    960
tcttaacaat tgatgatgta tgtaataggt ttgtgccaac gaaaactaat aggagaagat   1020
tgtacatcta aacacagtt cgtagttcgc taaaagcaat aattgagaaa cgagagaaag    1080
aggtacaatc tggaaaatca cacaatgaag atctgttggg tttgctaatg aaatctaatc    1140
aggaagaaca gcaagggaat aagaactcga acaaaggaat gagtacagag gatatgatag    1200
aagagtgcaa ctcttctat tttgctggtc aagagactac tgcaactttg ttaacatgga     1260
ctgcaattgt cttgactatg catccagatt ggcaagagaa agccaggaaa gaagttcttg    1320
aagtcattgg aaaagatgag cctaagtttg atcaactcaa ccatctaaag attgtaagaa    1380
gatactatcg tttcattc ccattcatac tttggaattt ttacatttga gtaaaccgtg      1440
tttaattata acaagtagaa tcacgaccca ccccataaac ttcaaattct agatctagga    1500
gtactagtga tttgaattct ggattcatct attaattaat aattgtgcta tatatgtagg    1560
taactatgat cttgcacgag gttctgaggt tatatccatc aggttctctt gttagagaaa    1620
caaacaaaaa gacaaagctt ggagagtatc caatcccagc aggtgcgcaa cttttagttc    1680
ctctacaaac aatccatcgc gatacagagg catggggaga agatgctcta attttcaatc    1740
```

```
cagaaaggtt ttcagaaggg gtatcaaaag catcaaagga cctgatgtac tttccgtttg    1800
gttggggttc tcggatatgc cttggaatga atgtttccat gattcaaggg aagcttgttt    1860
tggctaaaat cttacagaac tactcctttg agctttcccc ctcctatgct catggtccaa    1920
ccatgccagc tcttgttcta caaccacaat atggtgctcc tatgatcctt cgaaagctat    1980
catgatattg gtcaccctaa catgaatcaa taaatcactt ctctgtttcc tattgttgtg    2040 aactttctt cattctatcc acaaacagga ttgctgttta caccaatctc aagttcacat    2100
ca                                                                   2102
```

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 23
agcaatcaaa catgggtatt g                                              21

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 24
tgatgtgaac ttgagattgg tg                                             22

<210> SEQ ID NO 25
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 25
gagctctaga ggttaagagt ttgtgccaac g                                   31

<210> SEQ ID NO 26
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 26
ggatccatat ggctttctct tgccaatctg                                     30

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 27
tcgggtgagt tcagaaaacc                                                20

<210> SEQ ID NO 28
<211> LENGTH: 30
<212> TYPE: DNA

```
<213> ORGANISM: Artificial Sequence
<220> FEATURE:
<223> OTHER INFORMATION: Synthetic oligonucleotide primer

<400> SEQUENCE: 28
ggatccatat ggctttctct tgccaatctg                                           30
```